United States Patent
Saeki et al.

(10) Patent No.: US 9,566,028 B2
(45) Date of Patent: Feb. 14, 2017

(54) LANCET PRICKING DEVICE

(75) Inventors: Hideaki Saeki, Maniwa (JP); Hiroshi Hanafusa, Maniwa (JP); Kazuharu Seki, Setagaya-ku (JP); Teruyuki Abe, Shinagawa-ku (JP)

(73) Assignees: ASAHI POLYSLIDER COMPANY, LIMITED, Osaka (JP); IZUMI-COSMO COMPANY, LIMITED, Osaka (JP)

( * ) Notice: Subject to any disclaimer, the term of this patent is extended or adjusted under 35 U.S.C. 154(b) by 1375 days.

(21) Appl. No.: 13/394,624

(22) PCT Filed: Sep. 2, 2010

(86) PCT No.: PCT/JP2010/065029
§ 371 (c)(1),
(2), (4) Date: Apr. 26, 2012

(87) PCT Pub. No.: WO2011/030714
PCT Pub. Date: Mar. 17, 2011

(65) Prior Publication Data
US 2012/0203259 A1 Aug. 9, 2012

(30) Foreign Application Priority Data
Sep. 10, 2009 (JP) .................... 2009-209493

(51) Int. Cl.
*A61D 1/00* (2006.01)
*A61B 5/15* (2006.01)
*A61B 5/151* (2006.01)

(52) U.S. Cl.
CPC ....... *A61B 5/150603* (2013.01); *A61B 5/1513* (2013.01); *A61B 5/1519* (2013.01);
(Continued)

(58) Field of Classification Search
CPC ............ A61B 5/150603; A61B 5/150916; A61B 5/15019; A61B 5/150412; A61B 5/150549; A61B 5/150022; A61B 5/150618; A61B 5/150717; A61B 5/1519; A61B 5/15113; A61B 5/15117; A61B 5/1513; A61B 5/15142; A61B 5/15144; A61B 5/15186; A61B 5/150152; A61B 5/1411

See application file for complete search history.

(56) References Cited

U.S. PATENT DOCUMENTS

| 5,385,571 A | 1/1995 | Morita |
| 5,628,765 A * | 5/1997 | Morita ................. A61B 5/1411 604/136 |

(Continued)

FOREIGN PATENT DOCUMENTS

| CN | 101277646 | 6/2006 |
| JP | 2004-514496 | 5/2004 |

(Continued)

OTHER PUBLICATIONS

International Search Report issued Nov. 2, 2010 in International (PCT) Application No. PCT/JP2010/065029.

(Continued)

*Primary Examiner* — Richard Louis
(74) *Attorney, Agent, or Firm* — Wenderoth, Lind & Ponack, L.L.P.

(57) ABSTRACT

A lancet pricking device comprising a lancet, a launching spring and a lancet holder for housing therein the lancet and the launching spring. The lancet pricking device of the present invention is characterized in that the lancet comprises a lancet body, a lancet cap and a pricking needle, and the pricking needle is disposed in both the lancet body and the lancet cap; wherein the launching spring is attached to the lancet body, and the lancet body is secured by abutting (Continued)

against the lancet holder such that the launching spring is kept compressed before a pricking operation; and wherein, when the lancet cap is removed, the lancet body becomes capable of warping upon being pressed from an outside to cause the secured lancet body to be released.

12 Claims, 34 Drawing Sheets

(52) U.S. Cl.
CPC .... *A61B 5/15019* (2013.01); *A61B 5/150022* (2013.01); *A61B 5/15113* (2013.01); *A61B 5/15117* (2013.01); *A61B 5/15142* (2013.01); *A61B 5/15144* (2013.01); *A61B 5/150152* (2013.01); *A61B 5/15186* (2013.01); *A61B 5/150412* (2013.01); *A61B 5/150549* (2013.01); *A61B 5/150618* (2013.01); *A61B 5/150717* (2013.01); *A61B 5/150916* (2013.01)

(56) References Cited

U.S. PATENT DOCUMENTS

| | | | |
|---|---|---|---|
| 6,514,270 B1* | 2/2003 | Schraga | A61B 5/1411 606/181 |
| 2003/0130597 A1* | 7/2003 | Marshall | A61B 5/1411 600/583 |
| 2003/0153939 A1* | 8/2003 | Fritz | A61B 5/1411 606/181 |
| 2006/0058828 A1* | 3/2006 | Shi | A61B 5/1411 606/181 |
| 2007/0055297 A1 | 3/2007 | Fukuzawa et al. | |
| 2009/0069832 A1 | 3/2009 | Kitamura et al. | |
| 2009/0143810 A1 | 6/2009 | Kitamura et al. | |
| 2009/0275860 A1 | 11/2009 | Nakamura et al. | |

FOREIGN PATENT DOCUMENTS

| | | |
|---|---|---|
| JP | 2004-344292 | 12/2004 |
| JP | 2005-342325 | 12/2005 |
| WO | 2006/109452 | 10/2006 |
| WO | 2007/018215 | 2/2007 |
| WO | 2007/114094 | 10/2007 |
| WO | 2009/041110 | 4/2009 |

OTHER PUBLICATIONS

International Preliminary Report on Patentability issued Apr. 19, 2012 in International (PCT) Application No. PCT/JP2010/065029, together with English translation thereof.

* cited by examiner (a)

(b)

(a)

(b)

(a)

(b)

(a)

(b)

(a)

(b)

(c)

(a)

(b)

(a)

(b)

(a)

(b)

(a)

(b)

(a)

(b)

(a)

(b)

(a)

(b)

(a)

(b)

(a)

(b)

(a)

(b)

(a)

(b)

(a)

(b)

(a)

(b)

LANCET PRICKING DEVICE

TECHNICAL FIELD

The present invention relates to a pricking device. More specifically, the present invention relates to a lancet pricking device which is used for taking a sample of blood.

BACKGROUND ART

In order to measure a blood sugar level of a patient with diabetes, it is required to take a sample of the blood from the patient. The small amount of blood to be taken may be enough. Thus, a pricking device capable of taking a small amount of blood is used to measure the blood sugar level. The pricking device is generally composed of a lancet (see, for example, U.S. Pat. No. 5,385,571) and an injector. The lancet has a pricking needle capable of puncturing a predetermined region of the patient's body. The injector has a function of launching the lancet toward the predetermined region. The pricking device is set up for use by loading the lancet into the injector. Then, the lancet is launched toward the predetermined region by means of a plunger of the injector, whereby the predetermined region is pricked.

The pricking device used for taking blood from the patient with diabetes is required to be suitable in terms of hygiene and safety. In this regard, a particular attention must be paid to the handling of the used lancet. As for the used lancet, the tip of the pricking needle is exposed on a lancet body, and there may be the patient's blood adhered to the pricking needle due to the pricking. If the body of a person other than the subject of the blood sampling (for example, a nurse or medical practitioner who collects the blood sample) accidentally should touch the tip of the pricking needle, the body of such person may be pricked by the pricking needle. This will result in a wound of the body through which the patient's blood may enter the body (i.e. the body of the nurse or medical practitioner), and thus posing a risk of the infection disease.

The pricking device is also required to be suitable in terms of pricking performance in use. In particular, if a pricking operation is performed without a large deflecting of the pricking needle, the predetermined region of the patient's body can be surely pricked with the pricking needle. Thus, the pricking device with an improved pricking pathway of the needle is desired.

PRIOR ART DOCUMENTS

Patent Documents

Patent Document 1: U.S. Pat. No. 5,385,571

DISCLOSURE OF THE INVENTION

Problems to be Solved by the Invention

The present applicant has invented the following pricking device, and filed the application regarding such device (WO 2007/018215 A1, filed date: 8 Aug. 2006, title of the invention: "PRICKING DEVICE, AS WELL AS LANCET ASSEMBLY AND INJECTOR ASSEMBLY THAT CONSTITUTE THE PRICKING DEVICE"). Referring to the accompanying drawings, the lancet assembly and the injector assembly invented by the applicant will be briefly described below (note that the term "injector assembly" will be hereinafter referred to also as "injector"). FIG. 30 shows an external appearance of a lancet assembly 100', and FIG. 31 shows an external appearance of an injector 200'. As shown in FIG. 30, the lancet assembly 100' is composed of a lancet 101' and a protective cover 102'. As shown in FIGS. 32 and 33, the lancet 101' comprises a lancet body 104', a lancet cap 106' and a pricking needle 105'. The pricking needle 105' made of metal is disposed in both the lancet body 104' and the lancet cap 106' both of which are made of resin. The tip of the pricking needle 105' is covered with the lancet cap 106', and the lancet cap 106' and the lancet body 104' are integrally connected together by a weakened part 108'. As shown in FIGS. 30 and 33, the protective cover 102' is provided to enclose a part of the lancet body 104'. Such lancet assembly 100' is loaded into the injector 200', and then the lancet cap 106' is removed. By the removal of the lancet cap, the tip of the pricking needle 105' is exposed, and thereby the lancet can serve to prick.

The injector 200' shown in FIG. 31 can be used in combination with the lancet assembly 100' to launch the lancet body with the tip of the pricking needle 105' exposed. The injector 200' comprises a plunger 204' that is capable of engaging with a rear end portion of the lancet body to launch the lancet body in the pricking direction (see FIG. 34). As shown in FIG. 34, the lancet assembly 100' is loaded into the injector 200' by inserting the lancet assembly 100' into the injector 200' through a front end opening 214' of the injector 200'. As shown in FIG. 35, when the lancet assembly is inserted to some degree, a rear portion 116' of the lancet assembly 100' is held by tips 264' and 266' of the plunger 204'. Subsequently, when the insertion of the lancet assembly is continued, the plunger 204' is thrust backward so that the launching energy is stored. That is, the retraction of the plunger 204' can compress a spring (not shown) provided in the plunger 204'. This means that, when the compression of the spring is released, the plunger instantly moves forward to launch the lancet. FIG. 36 shows the injector 200' in the state where the plunger has retracted, and the launching energy has been stored therein.

After the loading of the lancet assembly 100' into the injector 200' is completed, the lancet cap 106' is removed to expose the tip of the pricking needle 105'. The removal of the lancet cap 106' will be described as follows:

As shown in FIGS. 32 and 33, the lancet body 104' and the lancet cap 106' are integrally connected together by the weakened part 108' disposed between the lancet body and the lancet cap. The weakened part 108' is broken by rotating the lancet body 104' and the lancet cap 106' around the pricking needle in the reverse direction to each other (see FIG. 36 showing an embodiment of rotating the lancet cap in the direction "G"), whereby the removal of the lancet cap 106' can be performed.

When the pricking operation is carried out, the front end opening 214' of the injector 200' is applied to a predetermined region to be pricked (for example, a finger tip). Subsequently, the press part 542' of a trigger component 514' is pushed. See FIG. 37. The pushing of the press part 542' results in an instantaneous expansion of the compressed spring, and thereby forcing the plunger 204' to move forwardly to prick the predetermined region with the pricking needle.

With respect to the pricking device as described above, it is desired that the pricking needle has a predetermined pathway. In particular, when the straight movement of the pricking needle is drastically degraded, the subject of the blood sampling feels more pain during the pricking. The pricking pathway of the needle is desired to be as straight as possible. Actually, however, the launched needle (particularly, the tip of the pricking needle) tends to undulate or ruffle, which makes it difficult to ensure the straight pricking pathway.

Furthermore, with respect to the pricking device as described above, there is a concern that the pricking needle which has been once used is re-used. That is, if the backward movement of the plunger 204' after the pricking operation is made possible by any means, "ready state for pricking" as shown in FIG. 37 can be obtained again, which leads to the possibility that the used lancet is again used for another pricking.

The present invention has been devised in view of the above-mentioned circumstances. That is, an object of the present invention is to provide a pricking device which can prevent the re-use of the lancet which has been once used. Another object of the present invention is to provide a pricking device with an improved pricking pathway.

Means for Solving the Problems

In order to achieve the above objects, the present invention provides a lancet pricking device comprising:
a lancet;
a launching spring; and
a lancet holder for housing therein the lancet and the launching spring,
wherein the lancet comprises a lancet body, a lancet cap and a pricking needle, and the pricking needle is disposed in both the lancet body and the lancet cap;
wherein the launching spring is attached to the lancet body, and the lancet body is secured by abutting against the lancet holder such that the launching spring is kept compressed before a pricking operation (more specifically, an engagement part of the lancet body and an engaged part of the lancet holder, both of which are provided for securing the lancet holder, are in contact with each other such that the launching spring is kept compressed before the pricking operation); and
wherein, when the lancet cap is removed, the lancet body becomes capable of warping or inclining upon being pressed from an outside to cause the secured lancet body to be released.

In such lancet pricking device, when the securing of the lancet body is released, the compressed launching spring is also released to expand, and thereby the "lancet body with the exposed pricking needle" is launched in the direction of pricking. The lancet pricking device of the present invention preferably has an elastic portion in the lancet body. The elastic portion serves to cause the lancet body to effectively warp when the body is pressed from the outside. The elastic portion also serves to slide on an inner wall surface of the lancet holder when the lancet body is launched to move in the pricking direction.

The present invention is characterized at least in that the lancet pricking device is substantially composed of three components, i.e., "lancet", "lancet holder" and "launching spring", and hence the device structure thereof is very simple.

The present invention is also characterized at least in that the lancet body is secured to the lancet holder such that the compressed state of the launching spring is maintained until the pricking operation, and that such securing of the lancet holder can be released through the removal of the lancet cap. Specifically, at a point in time before the pricking operation using the lancet pricking device of the present invention is performed (i.e., in the state where the tip of the pricking needle is covered with the lancet cap), at least a part of a wing portion of the lancet cap is positioned in a space formed between the lancet body and an inner wall surface of the lancet holder. As a result, there is prevented a warping of the lancet body, the warping being attributed to the pressing force from the outside. In other words, even when the lancet body is intended to be warped due to the pressing force from the outside, there is no space for a moving of the lancet body in the interior of the lancet holder (in particular, there is no space toward the warping direction of the lancet body to be pressed) because of the presence of the wing portion of the lancet cap. Thus, no warping of the lancet body can be substantially performed. This means that, when the needle is still covered with the lancet cap, the securing of the lancet body cannot be released, and thus the pricking needle is not launched. While on the other hand, after the lancet cap is removed, there is no presence of the wing portion between the lancet body and the inner wall surface of the lancet holder, and thus a space for the moving of the lancet body is generated in the interior of the lancet holder. As a result, the warping of the lancet body, which is attributed to the pressing force from the outside, can be performed. This means that, after the lancet cap is removed, the securing of the lancet body can be released, and thereby the pricking needle can be launched.

In a preferred embodiment, the lancet pricking device of the present invention has a further feature in that the lancet body is equipped with an elastic portion. It is preferred that such elastic portion "warps" or "squashes" when the lancet body warps due to the pressing force applied thereto. In other words, it is preferred that the releasing of the secured lancet body is facilitated mainly by the warping of the elastic portion, such warping being attributed to the pressing force from the outside.

It is preferred that the elastic portion of the lancet body, upon the pricking, slides on the inner wall surface of the lancet holder while being in contact with such inner surface. The sliding of the elastic portion enables the pricking pathway of the needle to become as straight as possible. In particular, the warping of the sliding elastic portion serves to effectively correct the pricking pathway so as to make it straight, which improves the pricking pathway of the needle.

In a preferred embodiment, the elastic portion has a hollow structure so as to effectively promote the warping of the elastic portion. In other words, it is preferred that the elastic portion has a circular or ring-like shape with its center part removed).

The term "elastic portion" as used herein means that a member, part or portion capable of being deformed by applying the external force thereto, and also capable of being returned to its "original form" or "similar form to the original one" after removing such external force.

The term "warp" or "warping" as used herein regarding the lancet body substantially means various types of movements (or displacements) in which the lancet body is moved (or displaced) in an interior space of the lancet holder. Thus, by way of example, the phrase "lancet body warps"/"warping of lancet body" as used therein means that the lancet body inclines within the lancet holder. Especially it means that a tip section of the lancet body inclines with respect to the axis line of the holder.

In a preferred embodiment, the inner wall surface of the lancet holder is provided with a tapered portion. The elastic portion of the lancet body, upon the pricking, slides on the tapered portion while being in contact with such tapered portion.

In another preferred embodiment, the lancet holder is provided with a trigger portion. In this embodiment, when the trigger portion is pushed toward the inside of the lancet holder after the removal of the lancet cap, the lancet body is forced to warp by a pressing force derived from the pushed trigger portion. This results in a ceasing of engagement between an engagement part of the lancet body and an engaged part of the lancet holder, both of which are provided for securing the lancet body. At a point in time before the pricking operation is performed, it is preferred that the front end of the trigger portion is substantially in a complementary engagement with an edge face defining an opening of the lancet holder. It is also preferred that, while the trigger portion is inwardly pushed in the pricking operation, at least a part of a periphery of the trigger portion abuts against an edge portion defining the trigger opening of the lancet holder, and thereby the warping of the lancet body is restricted. This means that an excessive warping of the lancet body is preferably prevented by restricting the pushed degree of the trigger at the time of pricking.

In a further preferred embodiment, the lancet body is provided with a projection "a" for adjusting a pricking depth, whereas the trigger portion is provided with a projection "b" for adjusting the pricking depth. In this embodiment, upon the pricking, the projection "a" of the lancet body makes contact with the projection "b" of the trigger portion, and thereby a protruding length of the pricking needle from an opening end of the lancet holder is restricted. It is preferred in this embodiment that the projection "a" for adjusting the pricking depth is capable of warping in a forward-backward direction (which is approximately equal to "pricking direction and opposite direction thereto"). It is further preferred that an auxiliary projection is provided in the lancet body to be located behind the projection "a". When the projection "a" warps backward due to the contacting (abutting) of the projection "a" of the lancet body onto the projection "b" of the trigger portion, the projection "a" is supported by the auxiliary protrusion.

The lancet pricking device of the present invention is also characterized in that it has such a structure that the pricking needle which has been already used for the pricking cannot be used again. Specifically, at a point in time before the pricking operation is performed, a forward side of the engagement part of the lancet body is in engagement with a backward side of the engaged part of the lancet holder, and thereby the lancet body is secured by abutting against the lancet holder; whereas at a point in time after the pricking operation is performed, a backward side of the engagement part of the lancet body is capable of making contact with a forward side of the engaged part of the lancet holder. Thus, even if the lancet body is intended to go backward to obtain the compressed state of the launching spring again after the pricking, the backward side of the engagement part of the lancet body makes contact with the forward side of the engaged part of the lancet holder, and thereby the further backward movement of the lancet is inhibited. Namely, due to the contacting of the backward side of the engagement part of the lancet body onto the forward side of the engaged part of the lancet holder, the lancet body cannot be returned to its pre-pricking state.

Effect of the Invention

The lancet pricking device of the invention is substantially composed of three parts, i.e., "lancet", "lancet holder" and "launching spring". Thus, the structure of the device is very simple and has the small size as a whole. Specifically, the lancet pricking device of the present invention has such a relatively simple structure that the "lancet" and the "launching spring" are housed in the lancet holder, and also the size of the lancet holder, which size determines the entire size of the device, substantially corresponds to the small size of the lancet. As a result, the lancet pricking device of the present invention is not only easy to manufacture, but also excellent in a transport efficiency and a storage space thereof. Moreover, the lancet pricking device of the present invention has such a small size to enable a holding by the fingers, and thus actually has a satisfactory operability.

The lancet pricking device of the present invention has such a structure that the pricking needle which has been already used for the pricking cannot be used again. Thus, the pricking device of the present invention does not have the risk of re-using the pricking needle, and is desirable from a hygiene and safety standpoint. The user has no choice but to use the lancet pricking device of the present invention only as a "non-reusable/disposable type device", and thereby the hygiene for the subject of the blood sampling can be secured inevitably.

Further, in accordance with the lancet pricking device of the present invention, the elastic portion can achieve as linear a pathway as possible with respect to the pricking pathway of the needle upon the pricking. As a result, the pain felt by the person to be pricked (i.e., the subject of the blood sampling) can be effectively reduced at the time of the pricking. While not wishing to be bound by any theory, the reduced pain is believed to be attributable to a reduction of "adverse phenomenon of hollowing or scratching the pricked portion by the moving needle". From this point, the lancet pricking device of the invention can suppress "deviation" (or "jiggle") of the pricking needle as much as possible, which can stabilize the pricking pathway of the needle. Therefore, the pricking pathway of the needle becomes substantially constant even when being used by a different user, and thus there is provided such an advantageous effect that the fluctuations or variations of the pricking pathway, attributed to the different users, can be reduced.

BEST MODE FOR CARRYING OUT THE INVENTION

Figure 1:
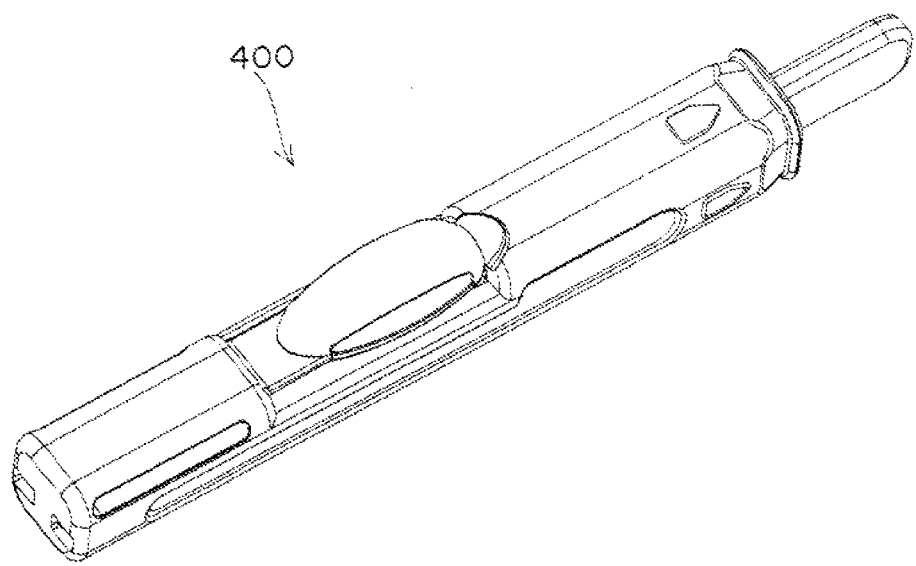
FIG. 1 is a view of an appearance of a lancet pricking device according to the present invention.
Figure 1:
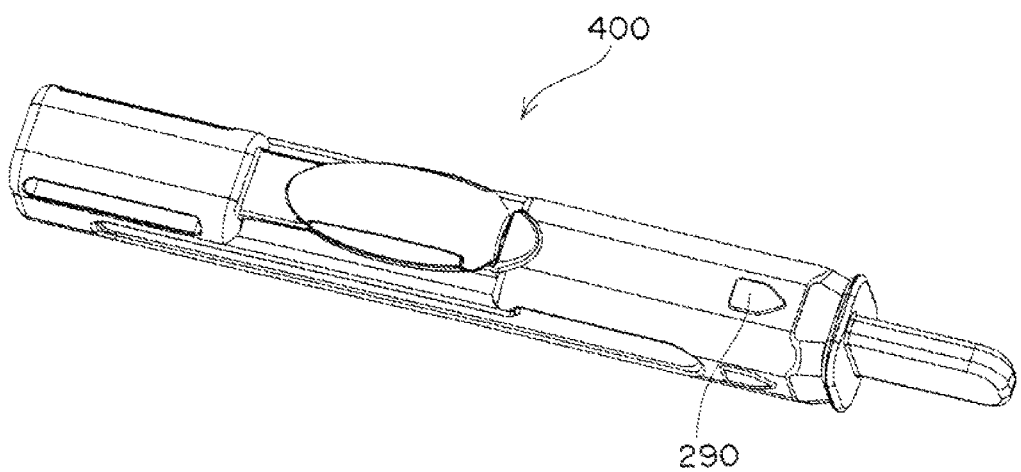

A lancet pricking device according to the present invention will be described in detail with reference to the accompanying drawings.

The term "direction" as used throughout the claims and description is defined as follows: The direction in which the pricking needle is launched for pricking is regarded as a "forward" direction. The reverse direction thereto is regarded as a "backward" direction. Such directions and also "transverse direction" are illustrated in the drawings. The "pricking direction" substantially means the direction in which the pricking needle moves toward the region to be pricked in the body of the subject of blood sampling, and thus corresponds to a "forward direction".

<<Basic Structure of Lancet Pricking Device>>

(Basic Structure)

Figure 2:
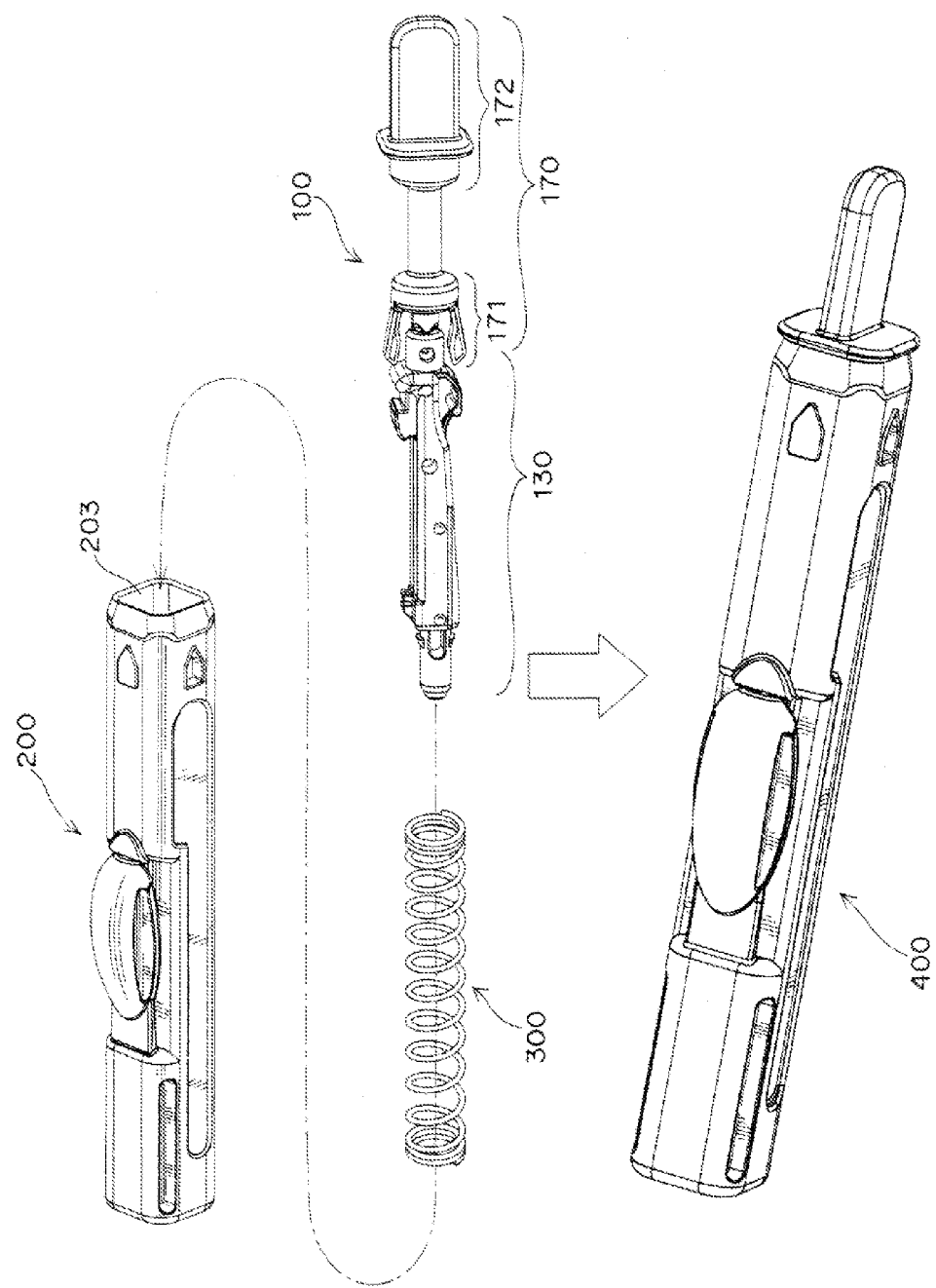
FIG. 2 shows an appearance view and an exploded perspective view of a lancet pricking device according to the present invention.

FIGS. 1 and 2 show a lancet pricking device 400 according to the present invention. FIG. 1 shows the appearance of a lancet pricking device 400. FIG. 2 shows an exploded view and a development view of the lancet pricking device 400. As shown in FIG. 2, the lancet pricking device 400 according to the present invention is mainly composed of a "lancet 100", "lancet holder 200" and "launching spring 300".

Figure 3:
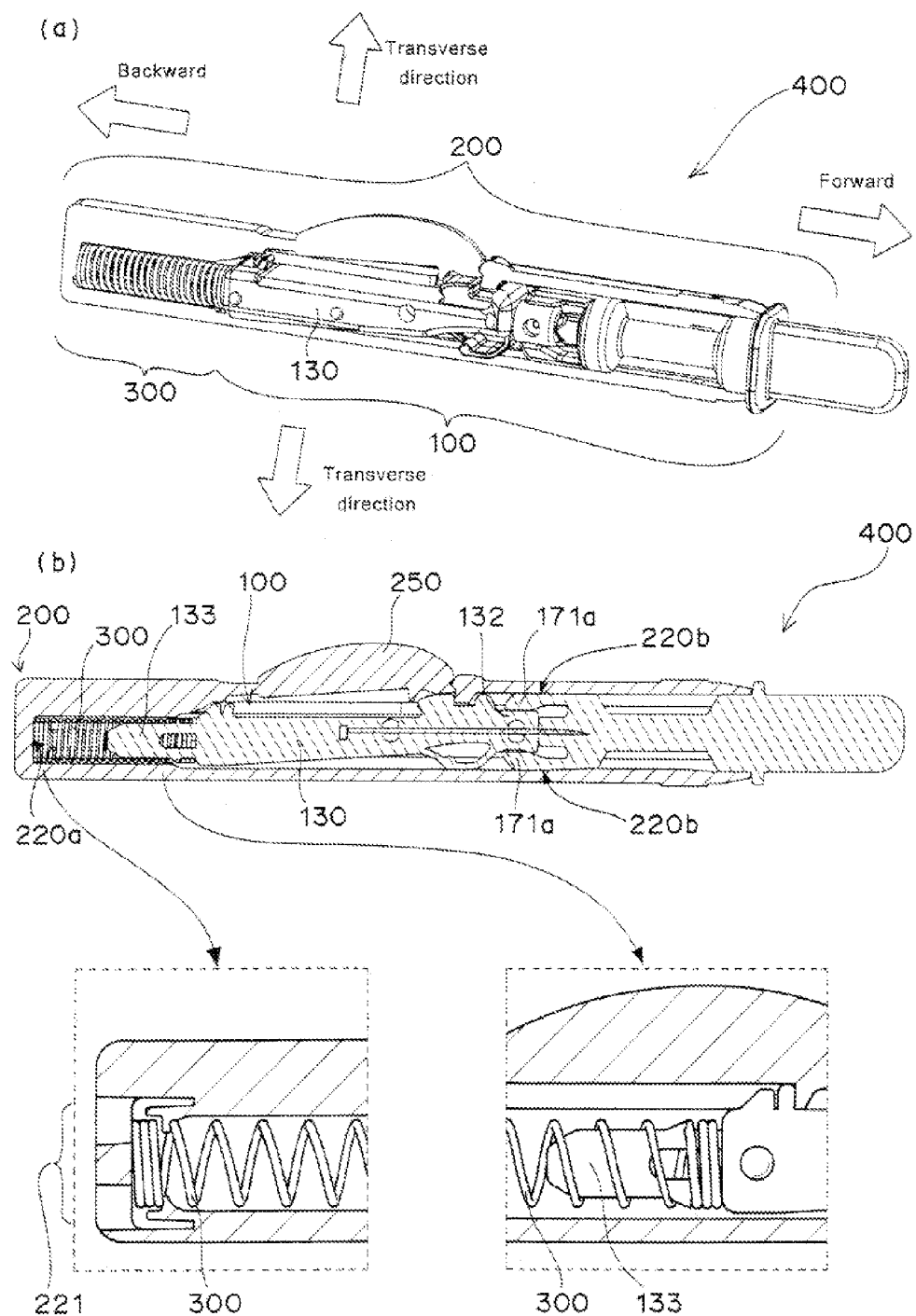
FIGS. 3(a) and 3(b) are a perspective view and a cross-sectional view showing an internal structure of a lancet pricking device according to the present invention.

As shown in FIG. 3, the lancet pricking device 400 of the present invention has such a structure that the lancet 100 and the launching spring 300 are housed in the lancet holder 200. Specifically, as shown in FIG. 3, the lancet 100 (except for a holding portion 172 of a lancet cap) and the launching spring 300 are housed in the lancet holder 200 such that the launching spring 300 is held between the lancet 100 and the inner wall surface of the lancet holder 200. More specifically, as shown in FIG. 3(*b*), one end of the launching spring 300 is attached to a rear end 133 of the lancet 100 in the lancet holder 200, and the other end of the launching spring 300 is attached to a fitting portion 221 provided at a rear end-sided inner wall surface 220*a* of the lancet holder 200. As can be seen by comparison between FIG. 2 and FIG. 3, the launching spring 300 inside the lancet holder 200 is in a compressed state between the "lancet 100" and the "rear end-sided inner wall surface of the lancet holder 200". In other words, in the lancet pricking device 400 of the present invention, a lancet body 130 is secured (or locked) to the lancet holder wherein the body is in abutment against the holder such that the launching spring 300 attached to the lancet body 130 is kept compressed.

In the following, components or parts regarding the lancet pricking device 400 will be described.

(Lancet Holder)

Figure 4:
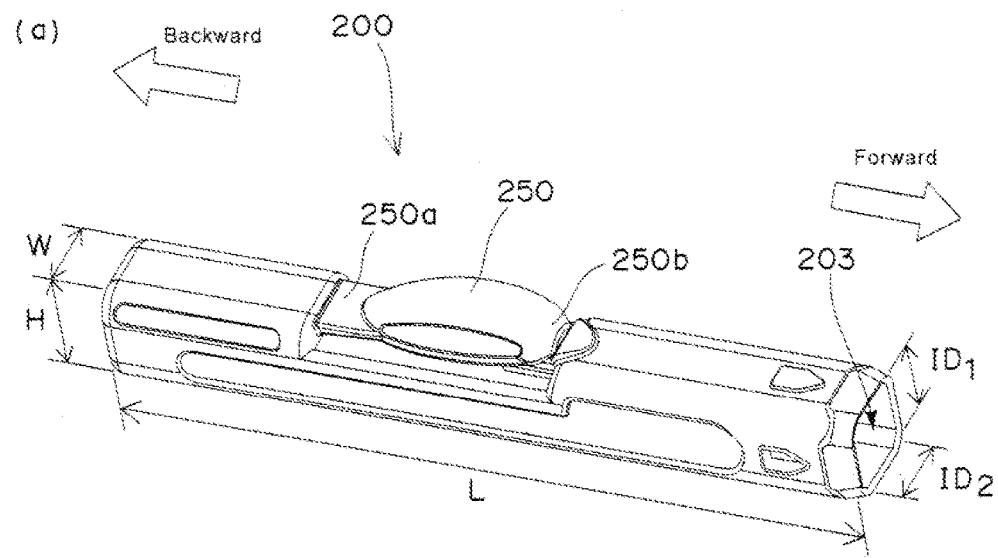
FIGS. 4(a) and 4(b) are a perspective view and a cross-sectional view of a lancet holder used in the lancet pricking device.
Figure 4:
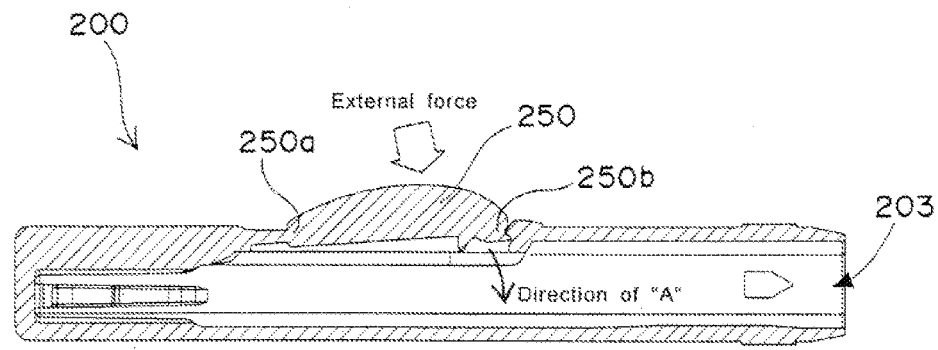

The lancet holder 200 has, as a whole, a shape of square box or square tube as shown in FIG. 4, for example. The lance holder has small dimensions. For example, the dimensions (L, H, W, $ID_1$, $ID_2$) shown in FIG. 4 regarding the lancet holder 200 may be, but not limited to, as follows: "L" is in the range of 40 to 60 mm (for example, about 50 mm), "H" is in the range of 7 to 11 mm (for example, about 11 mm), "W" is in the range of 7 to 11 mm (for example, about 7 mm), "$ID_1$" is in the range of 5 to 8 mm (for example, about 5 mm) and "$ID_2$" is in the range of 5 to 8 mm (for example, about 5 mm). The shape of the lancet holder 200 is not limited to the square box or square tube, and may be a cylinder. The lancet holder 200 may be formed of any kind of resin material which is used for lancets in general. As shown in FIG. 4, the lancet holder 200 is provided with an opening end 203. The opening end 203 serves as not only a portion into which the lancet 100 and the launching spring 300 can be inserted and thus set upon assembly of the pricking device, but also a portion applied to the region (e.g., finger) to be pricked at the time of pricking operation.

Typically, the lancet holder 200 is equipped with a trigger portion 250 as shown in FIG. 4. The trigger portion 250 is used for the pricking operation. When pressed from the outside, the trigger portion 250 functions to launch the pricking needle (more specifically, launch the lancet body equipped with the pricking needle). The trigger portion 250 has its rear end 250*a* integrally formed with a wall of the lancet holder, and its front end 250*b* serving as a free end. Accordingly, when pushed from the outside, the trigger portion 250 can move in the direction toward the inside of the holder (in the direction represented by the arrow "A" of FIG. 4(*b*)) with the rear end 250*a* serving as a pivot point of the movement. That is, the front end 250*b* of the trigger portion is forced to move toward the inside of the holder, and thereby a pushing of the lancet 100 disposed within the holder is performed.

(Lancet)

Figure 5:
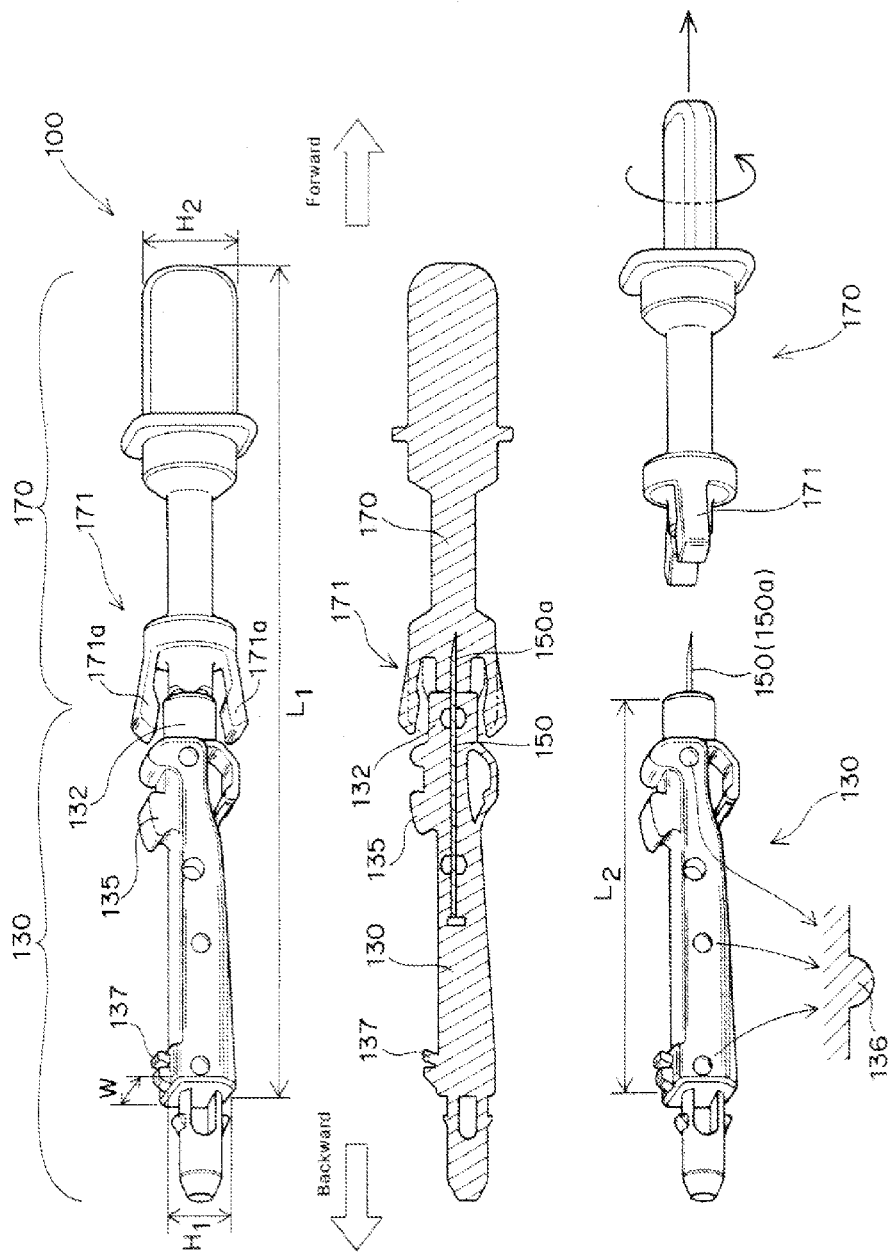
FIG. 5 is a perspective view, a cross-sectional view and an exploded view of a lancet used in the lancet pricking device.
Figure 6:
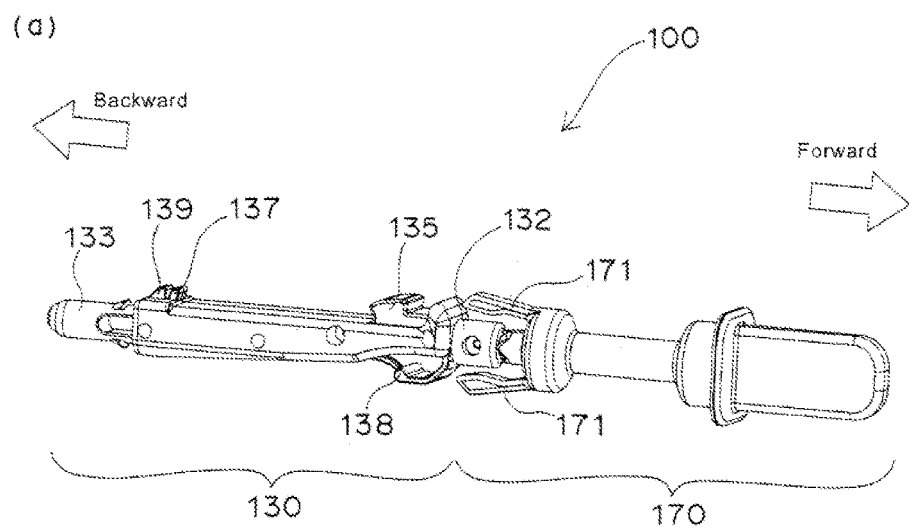
FIGS. 6(a) and 6(b) are perspective views of a lancet used in the lancet pricking device.
Figure 6:
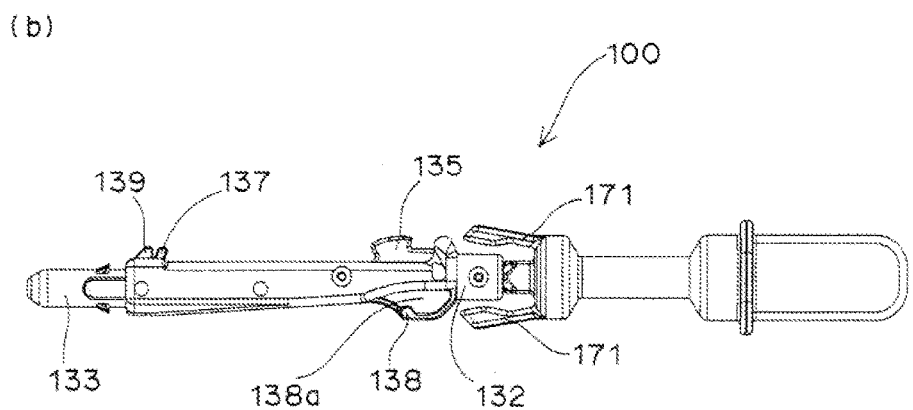

The lancet 100 used in the lancet pricking device 400 is shown in the perspective views and the cross-sectional views of FIGS. 5 and 6 (in which FIGS. 6(*a*) and 6(*b*) are diagrams of the lancet 100 respectively viewed from different sides). Similarly to the lancet holder 200, the lancet 100 is also small, and has such a size as to be housed in the lancet holder 200. For example, the dimensions ($L_1$, $L_2$, $H_1$, $H_2$, W) shown in FIG. 5 regarding the lancet may be, but not limited to, as follows: "$L_1$" is in the range of 40 to 60 mm (for example, about 55 mm), "$L_2$" is in the range of 20 to 40 mm (for example, about 30 mm), "$H_1$" is in the range of 3 to 5 mm (for example, about 3 mm), "$H_2$" is in the range of 4 to 8 mm (for example, 5 mm) and "W" is in the range of 4.5 to 8.2 mm (for example, about 4.8 mm). As shown in FIG. 5, the lancet 100 comprises the lancet body 130, the lancet cap 170 and the pricking needle 150 (especially, see FIG. 5 as to the pricking needle 150). The pricking needle 150 is, for example, a metal needle. The pricking needle 150 is situated in both the resin lancet body 130 and the resin lancet cap 170 wherein the tip 150*a* of the pricking needle 150 is covered with the lancet cap 170, as shown in the cross-sectional view of FIG. 5. It is preferred that the lancet body 130 and the lancet cap 170 are integrally connected to each other via only a small contact portion. The lancet 100 can be formed of resin (such as polyethylene, polypropylene or the like) by inserting the pricking needle 150 into a die, in a so-called insert molding process. In this case, the contact portion can be formed upon carrying out the insert molding process. Accordingly, the contact portion can be formed of the same resin as that of the lancet cap 170 and the lancet body 130. The contact portion is required to be broken upon removing the lancet cap. Thus, the contact portion can be referred to as a "weakened portion" or "easily broken portion". The contact portion may have a notch so that the contact portion can be easily broken. In some cases, the contact portion may be cut off in advance. No contact portion may also be provided in the lancet. As long as the lancet cap can be "twisted" to expose the tip 150*a* of the pricking needle 150 in the lancet body 130, the form of the contact portion is not limited to the specific one.

The lancet cap 170 comprises a wing portion 171 extending backward. The wing portion 171 is preferably composed of a pair of parts as shown in FIGS. 5 and 6. When the wing portion 171 is composed of the pair of parts, the respective parts of the wing portion 171 extend backward so as to be symmetric to each other with the center axis of the lancet 100 (i.e., the axis along the longitudinal direction of the lancet 100 or pricking needle 150) as shown in these figures. It is preferred that the wing portion 171 extends backward to reach a tip section 132 of the lancet body 130 as shown in FIGS. 5 and 6. In other words, the respective parts of the wing portion 171 preferably extend to such a position as to sandwich the tip section 132 of the lancet body therebetween before the twist operation of the lancet cap 170 is performed. When the lancet 100 with such a form is provided inside the lancet holder 200 (that is, in the lancet pricking device before the pricking operation), a tip 171*a* of the wing portion 171 is positioned in a space or gap formed between the tip section 132 of the lancet body 130 and an inner wall surface 220*b* of the lancet holder (see FIG. 3(*b*)).

The body of the pricking needle 150 is fixed in the lancet body 130. At the time of the pricking operation, the lancet body 130 together with the pricking needle 150 is launched forward. As shown in FIG. 6, a spring-attachment portion 133 to which the launching spring is attached is provided at the rear end of the lancet body 130. The lancet body 130 is provided with an "engagement part 135 for securing the lancet provided inside the lancet holder" at its side. The lancet body 130 is also provided with a "projection (137) "a" for adjusting a pricking depth upon pricking" and an "auxiliary projection (139)".

Figure 7:
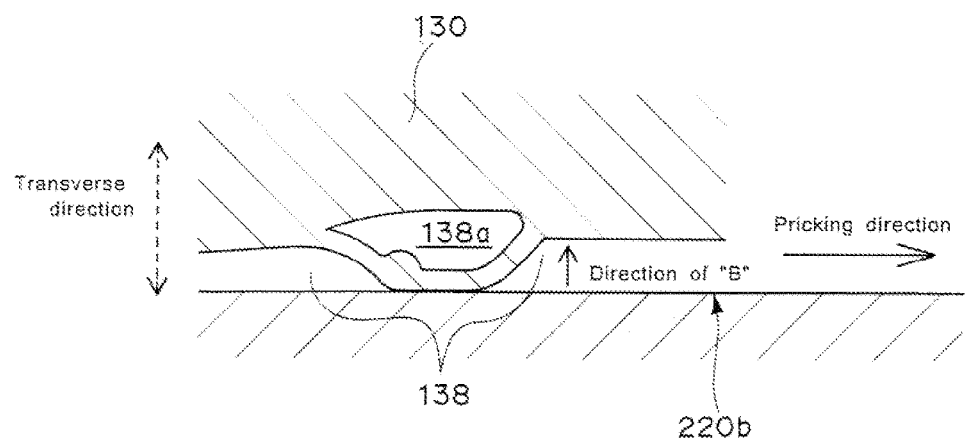
FIG. 7 is a schematic cross-sectional view showing an elastic portion provided in a lancet body.

The lancet body 130 used in the present invention is preferably provided with an elastic portion 138. The elastic portion 138 can serve to improve the straight shot of the pricking needle 150 upon the pricking (namely improve a straight pricking pathway). The elastic portion 138 can be deformed by applying the external force thereto. The elastic portion 138 may have any form as long as it can be returned to its "original state" or "state similar to the original state" after removing the applied external force therefrom. For example, the elastic portion 138 has a cavity 138*a* therein as shown in FIG. 6(*b*). That is, the elastic portion may have a hollow structure. It is preferred that the elastic portion is made of resin. The resin elastic portion may be formed of any kind of resin material that is used for lancets in general. For instance, the elastic portion may be formed of resin material such as polyethylene and polypropylene. When the external force from the outside (in the direction of "B" as shown in FIG. 7) is applied, the elastic portion with the hollow structure can be compressed so as to reduce its size in the applied direction of the external force. When being released from the external force, the elastic portion can be returned to its original shape. The cavity 138*a* of the elastic portion with the hollow structure is not limited to the specific one shown in the figures. For example, the cavity 138*a* may have a slit-like shape elongated in the direction of pricking, or may have a flat shape (i.e., a rectangular cross-section shape or a generally parallelogram cross-section shape) or the like.

(Launching Spring)

Figure 8:
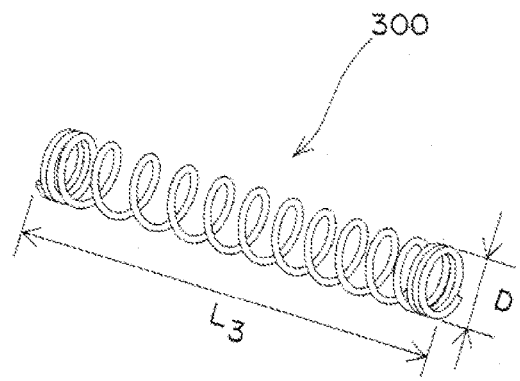
FIG. 8 is a perspective view of a launching spring used in the lancet pricking device.

The launching spring 300 is shown in the perspective view in FIG. 8. The launching spring 300 serves to shoot, fire or launch the needle as suggested by its name. In other words, the launching spring 300 is one that generates an impellent force for launching the pricking needle (i.e., "lancet body with the pricking needle exposed") or a drive force for pricking. As described above, the compressed spring 300 is provided between the "rear end-sided inner wall surface 220*a* of the lancet holder 200" and the "lancet 100" (see FIG. 3). The launching spring 300 is preferably made of metal. For instance, the spring 300 may be a metallic coil spring. The size of the launching spring 300 is not limited to a specific one as long as it can be housed in the lancet holder. For example, the launching spring 300 may have a length ($L_3$, D), at the point in time when it is not compressed as shown in FIG. 8, but not limited to, of $L_3$=15 to 25 mm (for example, about 20 mm) and D=2 to 5 mm (for example, about 3 mm).

<<Entire Structure and Function of Lancet Pricking Device>>

(Securing of Lancet Body)

Figure 9:
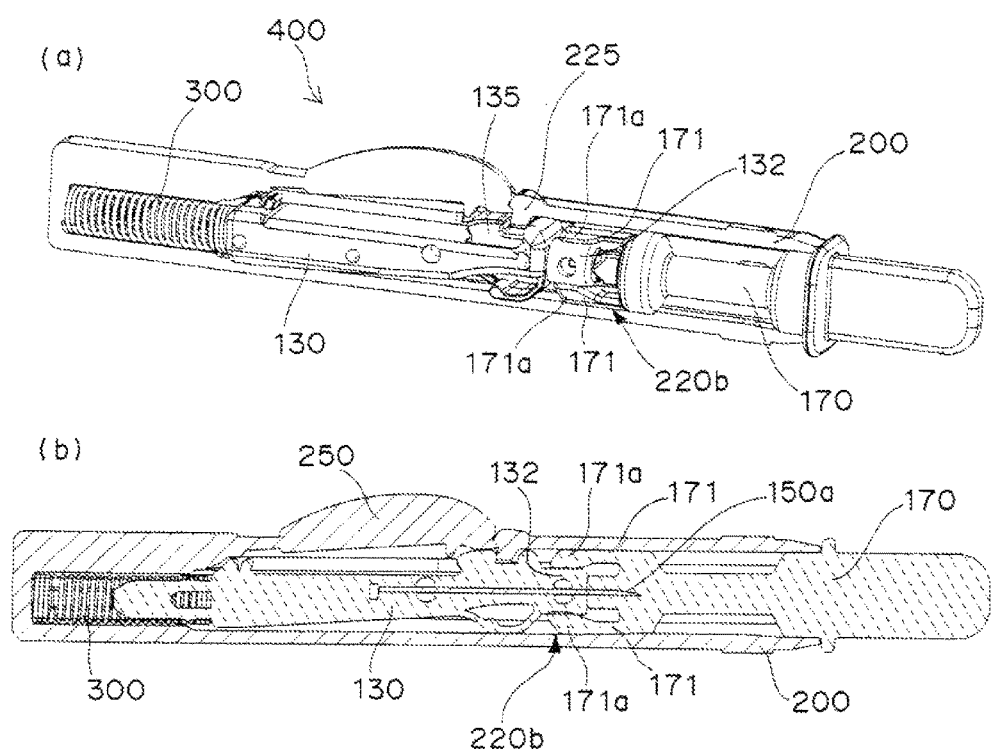
FIGS. 9(a) and 9(b) are a perspective view and a cross-sectional view showing an internal structure of a lancet pricking device according to the present invention at a point in time before the device is used.

In the lancet pricking device 400 of the invention, as shown in FIG. 9, the lancet body is in abutment against the lancet body, and thereby the lancet body 130 is secured to the lancet holder 200 such that the launching spring 300 is kept compressed. Such lancet pricking device 400 can be assembled by inserting the lancet 100 and the launching spring 300 into the lancet holder 200 from the opening end 203 thereof, followed by securing the lancet 100 to the lancet holder with the launching spring 300 thrust therein (see FIG. 2).

As shown in FIG. 9(*a*), the securing of the lancet body to the lancet holder is performed by abutting the "engagement part 135 of the lancet body 130" against the "engaged part 225 of the lancet holder 200". That is, the contacting of the engagement part 135 of the lancet body 130 with the engaged part 225 of the lancet holder 200 is performed while thrusting the lancet 100 backward within the lancet holder 200 to compress the launching spring 300. In the lancet holder 200, the forward force attributed to the compressed spring 300 acts on the lancet 100, and thereby the lancet 100 is forced to forwardly move. However, the forward movement of the lancet body 130 is locked by the abutting of the engagement part 135 of the lancet body 130 against the engaged part 225 of the lancet holder 200. It should be noted that the lancet body 130 is locked or secured to the lancet holder 200, whereas the lancet cap 170 is not locked or secured to the lancet holder 200, and thereby the lancet cap 170 can be removed prior to the pricking operation.

Figure 10:
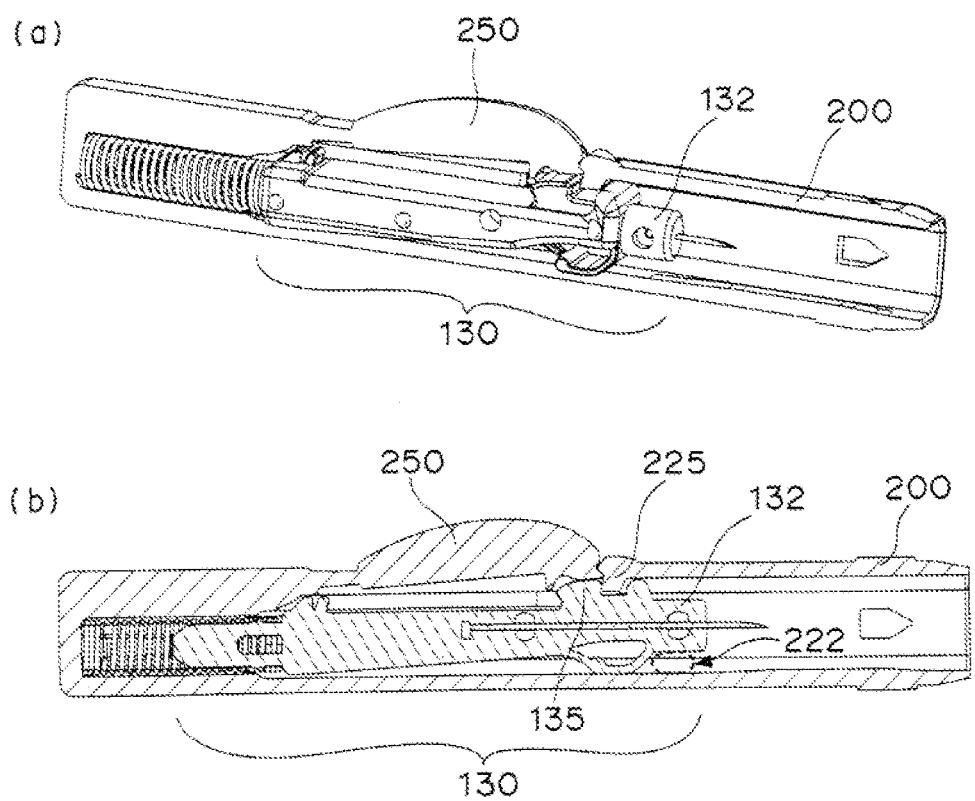
FIGS. 10(a) and 10(b) are a perspective view and a cross-sectional view showing an internal structure of a lancet pricking device at a point in time after a lancet cap is removed from a pricking needle.

As shown in FIG. 9, while the tip 150*a* of the pricking needle is covered with the lancet cap 170, at least a part of the wing portion 171 of the cap is positioned in a space formed between "part of the lancet body 130" and "inner wall surface 220*b* of the lancet holder". More specifically, as shown in FIG. 9(*b*), the tip 171*a* of the wing portion 171 is sandwiched between the "inner wall surface 220*b* of the lancet holder 200" and the "tip section 132 of the lancet body 130". As can be seen from the embodiment shown in FIG. 9, the "tip section 132 of the lancet body 130", the "tip 171*a* of the wing portion 171" and the "inner wall surface 220*b* of the lancet holder 200" establish intimate contacts with one another. Thus, the tip section 132 of the lancet body 130 cannot substantially move inside the holder even when being pushed in the transverse direction from the outside. This means that, even when the trigger 250 is pushed into the holder, the warping of the lancet body cannot be performed. As a result, there is no ceasing of the abutting between the engagement part 135 of the lancet body 130 and the engaged part 225 of the lancet holder 200. While on the other hand, when the lancet cap 170 is removed as shown in FIG. 10, the wing portion thereof is also removed, and thereby generating a space around the tip section 132 of the lancet body 130 (see the "space" indicated by reference numeral 222 of FIG. 10(*b*)). In this case, the trigger portion 250 can be pushed toward the inside of the holder, and thereby the lancet body 130 is caused to warp. As a result, there is generated a ceasing of the abutting between the engagement part 135 of the lancet body 130 and the engaged part 225 of the lancet holder 200, which makes it possible to release the securing or locking of the lancet body.

Figure 11:
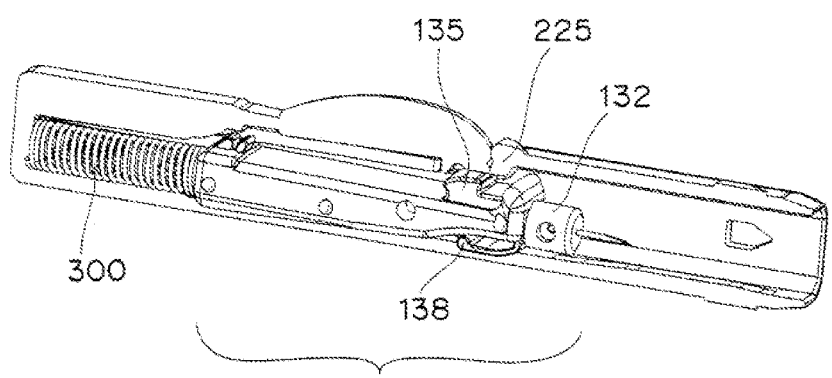
FIGS. 11(*a*) and 11(*b*) are a perspective view and a cross-sectional view showing the warped state of the lancet body.
Figure 11:
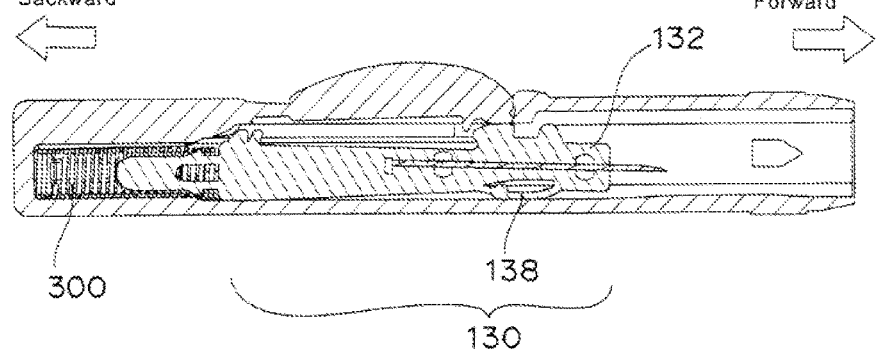

It is preferred that, as shown in FIG. 11, the lancet body 130 warps so that its front side inclines. More specifically, the lancet body 130 preferably warps such that the tip section 132 of the lancet body 130 inclines substantially in the same direction as the pushing direction of the trigger portion. In particular, it is preferred that, as shown in FIG. 11, the elastic portion 138 provided in the front section of the lancet body 130 "squashes" or "warps" to cause the tip section 132 of the lancet body 130 to incline in the pushing direction. The inclining of the tip section 132 of the lancet body 130 makes it possible to surely and readily cease the abutment between the engagement part 135 of the lancet body 130 and the engaged part 225 of the lancet holder 200 (see FIG. 11(*a*)). Such cease of the abutting causes the compressed spring 300 to expand, and thereby forcing "lancet body with the pricking needle exposed" to be launched in the pricking direction.

Figure 12:
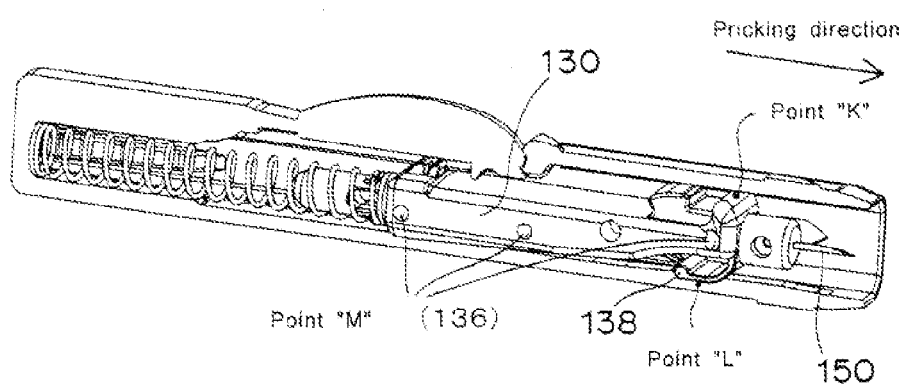
FIG. 12 is a perspective view and a transverse cross-sectional view of the embodiment of the lancet body moving in the pricking direction.
Figure 12:
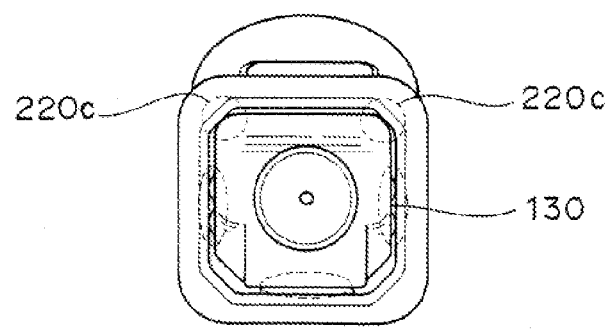

The "lancet body with the pricking needle exposed" is launched such that the pricking needle moves substantially along the center axis of the holder due to the restoring force or the like of the squashed or warped elastic portion 138. This means that "the lancet body with the pricking needle exposed", after being launched, moves in the pricking direction along the inner wall of the lancet holder. In other words, the lancet body moves forwardly in such a manner as to be guided by the inner wall surface of the lancet holder. More specifically, as shown in FIG. 12, the lancet body 130 moving in the pricking direction is in contact with the inner wall surface of the holder at points "K" and "L" in the vertical direction, while being also in contact with the inner wall surface of the holder at point "M" in the lateral direction. As for the point "K", it is preferred that the upper edge of the lancet body 130 is in contact with a chamfered part 220*c* of the inner wall's corner of the holder as shown in the cross-sectional view of FIG. 12. As for the point "M", it is preferred that bosses 136 provided on the sides of the lancet body 130 are in contact with the inner wall surface of the holder (also see FIG. 5 for understanding of the "boss 136").

(Improved Straight Pricking Pathway)

The "improved straight pricking pathway" of the lancet pricking device 400 will be described below. It is preferred in the lancet pricking device 400 of the present invention that the lancet body 130 is provided with the elastic portion 138 as described above (see, for example, FIG. 7 or 12). The provision of the elastic portion 138 can improve the straight pricking movement of the pricking needle 150 upon the pricking operation.

When the lancet body 130 equipped with the elastic portion 138 is launched to move in the pricking direction, the elastic portion 138 of the moving lancet body 130 slides on the inner wall surface 220b of the lancet holder (see FIG. 7). That is, when the lancet body with the pricking needle moves in the pricking direction, the elastic portion provided in the lancet body also moves in the pricking direction in the same manner. During the movement of the lancet body, the elastic portion comes into contact with the inner wall surface of the lancet holder. In particular, the elastic portion is brought into contact with the inner wall surface of the lancet holder so as to receive the external force attributed to the inner wall surface of the lancet holder. Thus, the elastic portion can absorb the shock occurred in the launched pricking needle, so that the pricking needle moving in the pricking direction is stabilized. In other words, the moving elastic portion slides on the inner wall surface of the lancet holder, and thus the stress generated in the pricking needle can be relieved by a cushion effect of the elastic portion, even though the pricking needle probably receives some transverse force. As a result, a linear pricking pathway of the needle can be ensured.

Figure 13:
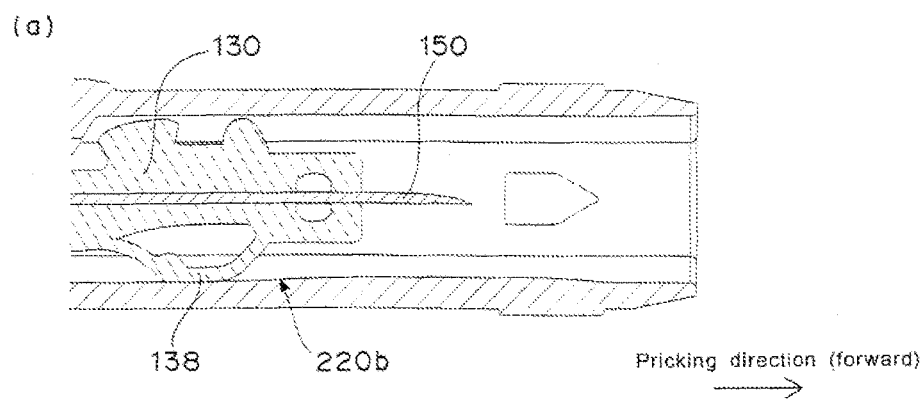
FIG. 13(*a*) is a cross-sectional view showing the embodiment of the lancet body moving forward upon pricking, FIG. 13(*b*) is a cross-sectional view showing the embodiment of the lancet body at the time of pricking, and FIG. 13(*c*) is a schematic view showing the embodiment of the elastic portion sliding on the tapered portion, while showing "decrease in inner diameter of a lancet holder at its tapered portion".
Figure 13:
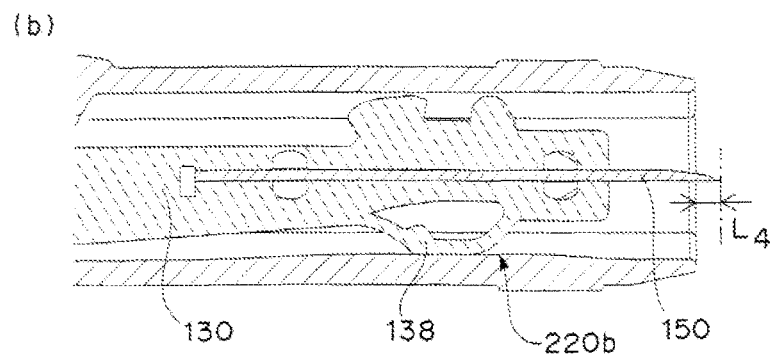
Figure 13:
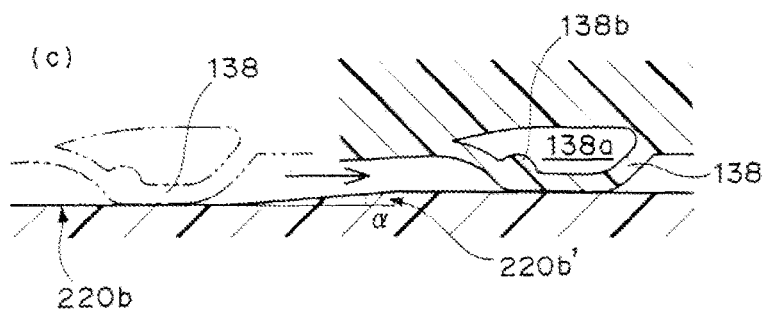
Figure 13:
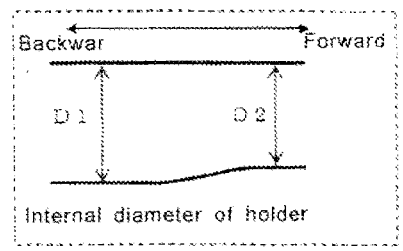

The "improved straight pricking pathway" will be described in more detail. FIG. 13(a) shows the embodiment of the lancet body 130 and the pricking needle 150 moving forward. FIG. 13(b) shows the embodiment of the device at the time of the pricking. As shown in FIGS. 13(a) and 13(b), the elastic portion 138 of the lancet body 130 moves forward while being in contact with the inner wall surface 220b of the lancet holder. That is, the elastic portion 138 of the moving lancet body 130 slides on the inner wall surface 220b of the holder. Upon pricking, the elastic portion 138 receives the force from the inner wall surface 220b of the holder to cause the "warping of the elastic portion 138". In particular, as shown in FIG. 13(c), the inner wall surface 220b of the lancet holder may have a tapered portion 220b' (i.e., "sloped portion"). In this case, the elastic portion 138 can effectively receive the force when it slides on the tapered portion 220b'. That is, the moving elastic portion tends to be easily warped by the tapered portion, so that the elastic portion effectively absorbs the shock of the lancet body upon the pricking operation, which can further stabilize the pricking pathway of the needle.

Figure 14:
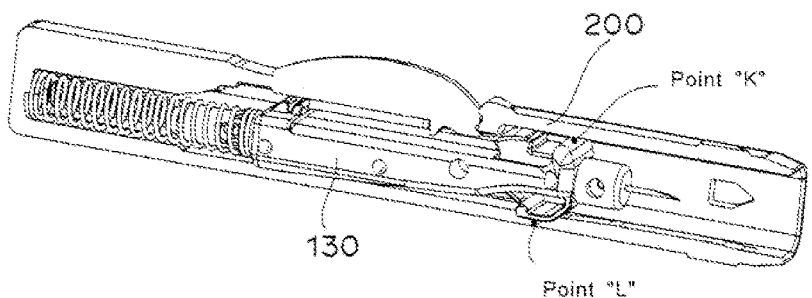
FIGS. 14(*a*) and 14(*b*) are a perspective view and a cross-sectional view showing the embodiment of the lancet body moving in the pricking direction.
Figure 14:
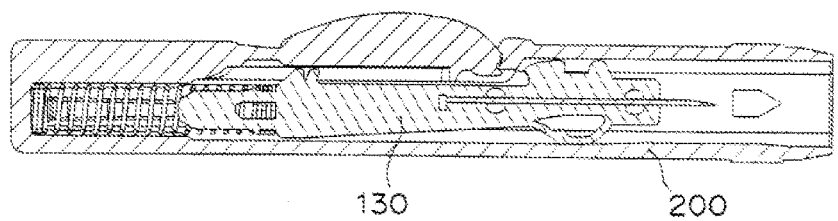

The functions of the elastic portion 138 will be described in more detail. The launched lancet body 130, which is moving in the pricking direction, is in contact with the inner wall of the hard lancet holder 200 at the points "K" and "L" as shown in FIG. 14. That is, the launched lancet body 130 moves while being in contact with the inner wall of the lancet holder. Thus, when the lancet body passes through a narrowed portion (i.e., tapered portion), the force received from the inner wall of the lancet holder becomes larger. In other words, as shown in FIG. 13(c), when the inner diameter of the holder is narrowed by the tapered portion 220b', the force acting on the lancet body from the outside to the inside thereof becomes larger due to the narrowing of the holder. As a result, the elastic portion 138 can be effectively caused to warp at the tapered portion 220b'. In this regard, the inner diameter of the holder is preferably reduced for example by about 0.1 to 20% due to the presence of the tapered portion 220b'. More preferably, the inner diameter of the holder is reduced by about 0.1 to 15% due to the tapered part 220b'. That is, a decrease ratio "R" of inner diameter of the lancet holder, which is indicated by the following formula, is preferably in the range of about 0.1 to 20%, more preferably in the range of about 0.1 to 15%:

$$R=(D1-D2)/D1 \times 100$$

where R (%) is a decrease ratio of inner diameter of the lancet holder, attributed to the tapered portion, D1 (mm) is an inner diameter of the holder, the diameter being positioned at the rear side with respect to the tapered portion (see FIG. 13(c)), and D2 (mm) is an inner diameter of the holder, the diameter being narrowed by the tapered portion (see FIG. 13(c)).

A protrusion 138b is preferably provided on an inner surface forming the cavity portion 138a of the elastic portion 138 in order to prevent the excessive deformation of the elastic portion (see FIG. 13(c)). This protrusion 138b can not only prevent the excessive deformation of the elastic portion, but also control the amount of deformation of the elastic portion 138 by adjusting the size of the protrusion 138b, and thereby the amount of the absorbed shock in the elastic portion can be appropriately adjusted. The elastic portion used in the present invention also contributes to the warping of the lancet body upon the launching of the lancet body (that is, at the time of pushing of the trigger portion). By appropriately changing the size of the protrusion 138b, the amount of the warping of the lancet body at the time of pushing of the trigger portion can be adjusted to a desired level.

(Structure of Trigger Portion)

The trigger portion 250 used in the lancet pricking device 400 of the present invention, and a structure associated therewith will be described below.

Figure 15:
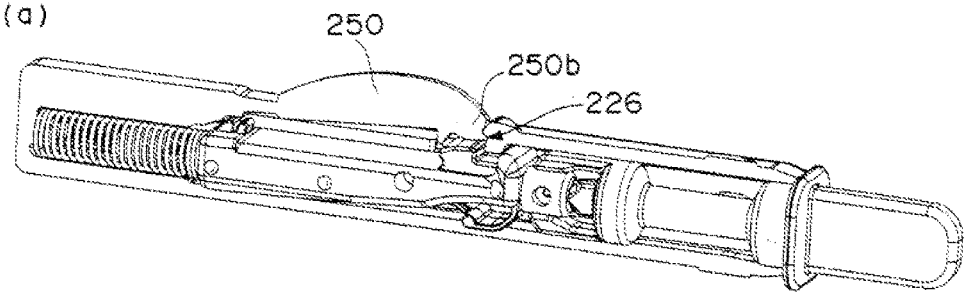
FIGS. 15(*a*) and 15(*b*) are a perspective view and a cross-sectional view showing the embodiment of the lancet pricking device at a point in time before the pricking operation is performed.
Figure 15:
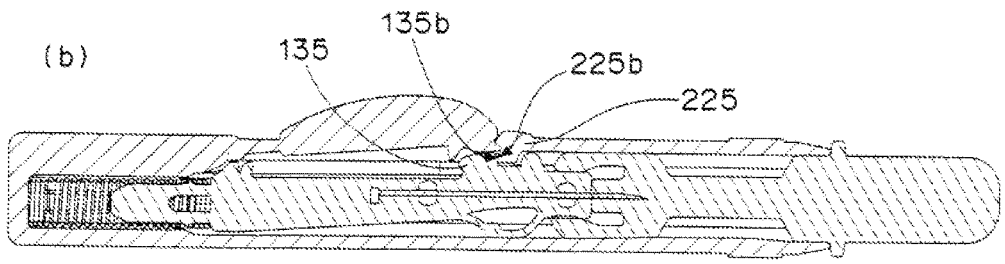
Figure 16:
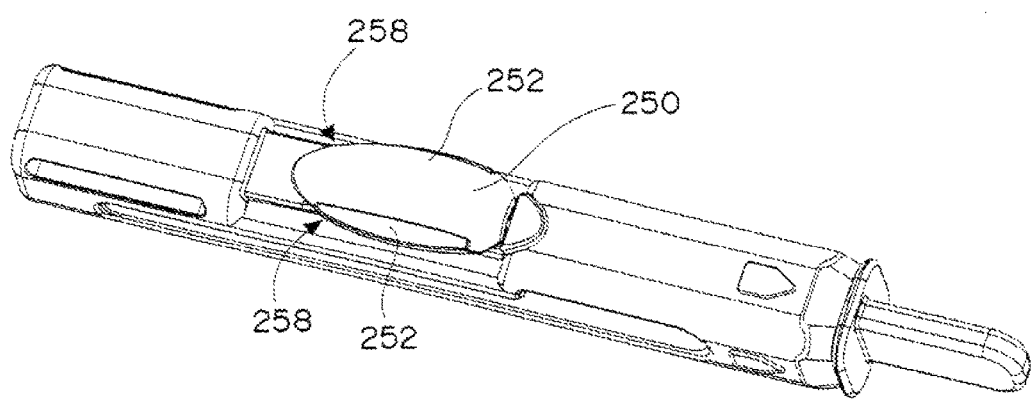
FIG. 16 is a perspective view showing an appearance of a trigger portion of the lancet pricking device.

As shown in FIG. 15, it is preferred that a front end 250b of the trigger portion 250 is substantially in a complementary engagement with an edge surface 226 defining a trigger opening of the lancet holder 200 before the pricking operation. Thus, even if an incidental force is applied to the trigger portion before the pricking, the trigger portion 250 is prevented from being unnecessarily pushed. It is preferred that, when the pushing of the trigger portion into the holder is performed for pricking, at least a part of the periphery of the trigger portion abuts against an edge portion defining the trigger opening of the lancet holder. Accordingly, the amount of the pushing of the trigger portion upon the pricking operation is controlled, which can prevent an excessive warping of the lancet body. With reference to FIG. 16, while the trigger portion 250 is pushed into the holder, an expanded part 252 of the trigger portion 250 is brought into abutment against an edge portion 258 defining the trigger opening of the lancet holder. Thus, the trigger cannot be further pushed into the holder any more, and as a result, the pushed amount of the trigger portion is restricted during the pricking operation.

(Pricking Depth Adjustment Mechanism)

Figure 17:
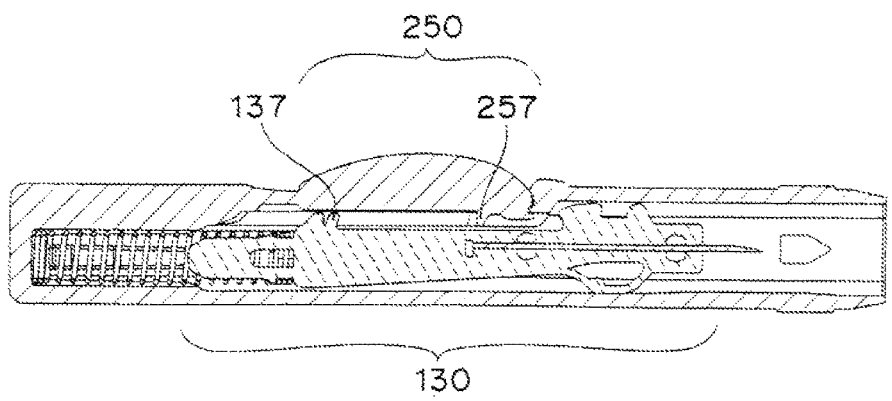
FIG. 17 is a cross-sectional view showing a component contributing to a pricking depth adjustment mechanism.
Figure 18:
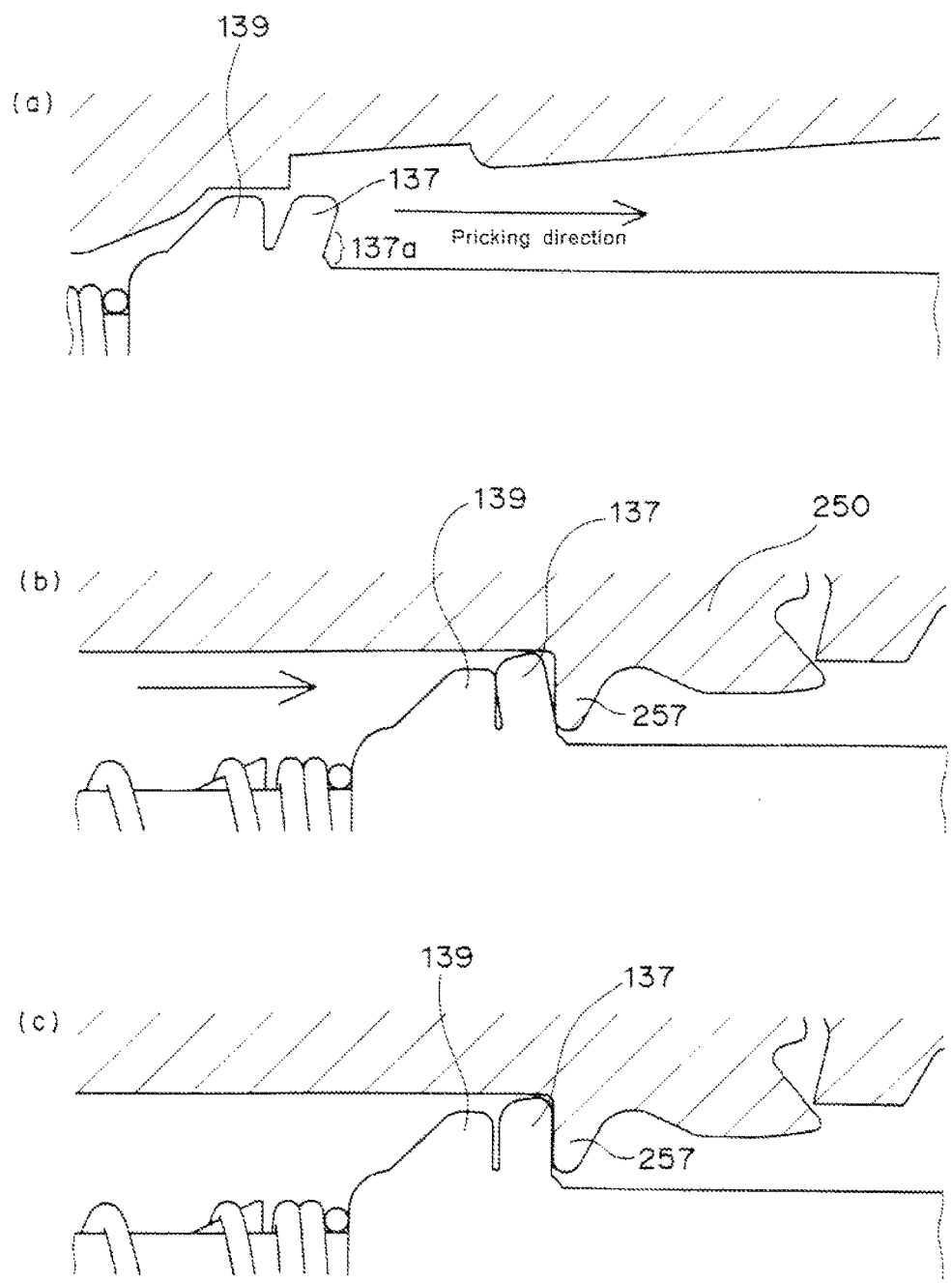
FIGS. 18(*a*) to 18(*c*) are schematic cross-sectional views showing the change in pricking depth adjustment mechanism over time upon pricking.

The lancet pricking device 400 of the present invention preferably has a pricking depth adjustment mechanism. Specifically, as shown in FIG. 17, the projection "a" (137) for adjustment of the pricking depth is provided in the lancet body 130, whereas the projection "b" (257) for adjustment of the pricking depth is provided in the trigger portion 250. As shown in FIGS. 18(a) to 18(c), the projection "a" (137) of the lancet body makes contact with or hits the projection "b" (257) of the trigger portion 250 upon the pricking operation, whereby the length of the pricking needle exposed from the open end of the lancet holder is defined or limited (see the reference numeral "$L_4$" of FIG. 13(b) for understanding of the "length of the pricking needle exposed from the open end"). That is, the collision between the projection "a" (137) and the projection "b" (257) restricts the forward movement of the pricking needle, making it possible to define the pricking depth (specifically, the length of the pricking needle protruding from the opening end 203 of the holder). Thus, the "pricking depth" can be adjusted by appropriately changing the "set position of the projection "a" (137) of the lancet body 130" and/or the "set position of the projection "b" (257) of the trigger portion 250". As can be seen from the embodiments shown in FIG. 18, the projection "a" (137) for adjustment of the pricking depth, which is provided in the lancet body, preferably has flexibility. In other words, it is preferred that the projection "a" (137) is capable of warping in a forward-backward direction. This can reduce the "undulating or ruffling phenomenon of the pricking needle" that is possibly caused by the collision between the projection "a" (137) and the projection "b" (257). When the projection "a" (137) of the lancet body collides with the projection "b" (257) of the trigger portion, the vibration of the undulating or ruffling pricking needle can be generated due to the collision (that is, the pathway for the pricking needle can be generally deflected). In this regard, the projection "a" (137), which is indirectly or directly connected to the pricking needle, can serve to effectively absorb the undulating or ruffling energy. It is preferred that, as shown in FIGS. 18(a) to 18(c), an auxiliary projection (139) is provided in the lancet body such that it is located behind the projection "a" (137). In such case, when the backward warping of the projection "a" (137) is performed due to the abutting of the projection "a" (137) against the projection "b" (257), the projection "a" (137) can be supported by the auxiliary projection (139).

The projection "a" (137), the projection "b" (257) and the auxiliary projection (139) may be formed of any kind of resin material as long as it can be used for the general lancet. The flexibility of the projection "a" (137) may be provided in terms of its material. Alternatively, the flexibility of the projection "a" (137) may be provided in terms of its structure. For example, in a case where the flexibility is provided in terms of the material, the projection "a" (137) may be formed of rubber or elastomer material. In a case where the flexibility is provided in terms of structure, a root of the projection "a" (137) may be reduced in size or may be elongated (see reference numeral "137a" in FIG. 18(a) for understanding of the root). Alternatively, the projection "a" (137) may also be entirely tapered such that its part closer to the tip of the projection is more increased in size.

(Re-Use Preventing Mechanism)

Figure 19:
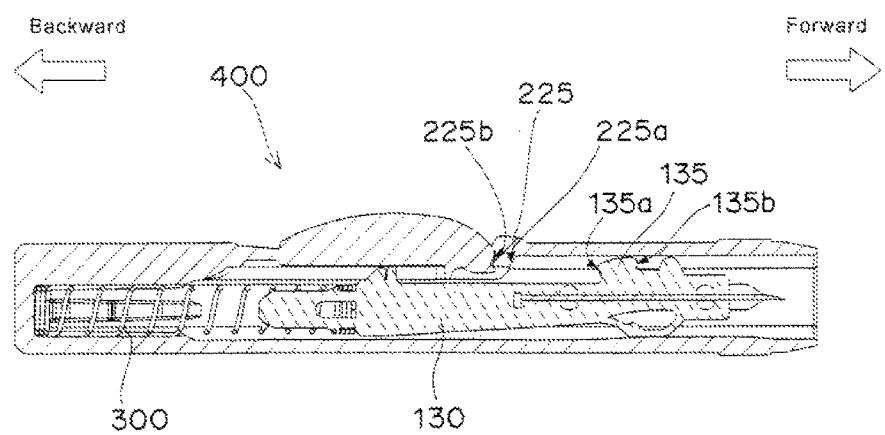
FIG. 19 is a cross-sectional view for explaining a re-use preventing mechanism.
Figure 19:
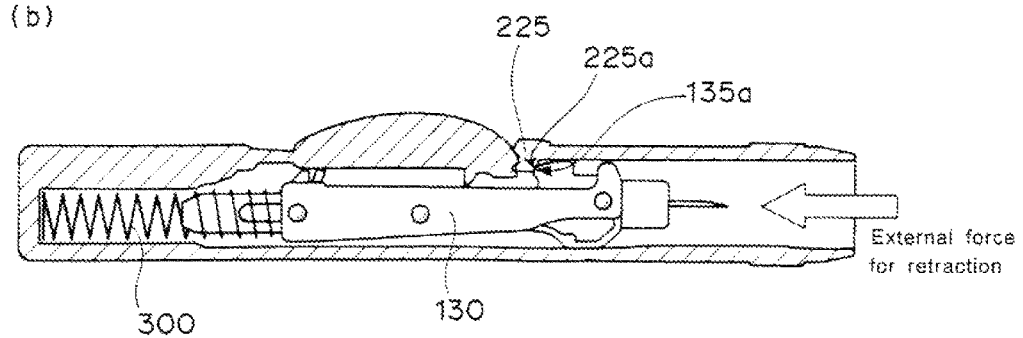

The lancet pricking device 400 of the present invention preferably has a re-use preventing mechanism. FIG. 19 shows an embodiment of the lancet pricking device 400 after the pricking operation. As shown in FIGS. 19(a) and 19(b), even if the lancet body 130 is forced to be moved backward so as to obtain the compressed state of the launching spring 300 again after the pricking operation, a backward side 135a of the engagement part 135 of the lancet body 130 makes contact with a forward side 225a of the engaged part 225 of the lancet holder. As a result, the lancet body 130 cannot be moved backward any more after the contacting of the engagement part 135 with the engaged part 225. That is, the used pricking device cannot be returned to its original state of pre-pricking. This prevents a re-use of the used pricking needle, which is very desirable from the viewpoint of hygiene and safety. The lancet pricking device of the present invention having this kind of re-use preventing mechanism can be referred to as a "single use device". Whereas, after the pricking operation, the "backward side 135a of the engagement part 135 of the lancet body 130" is capable of making contact with the "forward side 225a of the engaged part 225 of the lancet holder 200", before the pricking operation, the securing of the lancet body is preferably performed by abutting the "forward side 135b of the engagement portion 135 of the lancet body 130" against the "backward side 225b of the engaged portion 225 of the lancet holder 200" (see FIGS. 19 and 15).

(Pricked Pain Reducing Mechanism)

In accordance with the lancet pricking device of the invention, at least one of the following effects (A) to (D) is provided to reduce the pain felt by the pricked subject upon pricking.

(A) Straight Movement Effect of Pricking Needle by Elastic Portion

The lancet pricking device of the present invention has a function of correcting the track of the pricking needle to make it as straight as possible upon pricking by means of the "elastic portion". While not wishing to be bound by any theory, the hollowing or scratching of the pricked region by the pricking needle is reduced by the straight track of the pricking needle to thereby reduce the pain felt by the subject pricked upon the pricking. Likewise, the device of the present invention also improves the straight movement of the pricking needle moving backward after the pricking operation. Since the elastic portion moving backward after the pricking operation also slides on the inner wall surface of the holder, the shock received in the pricking needle can be effectively absorbed by the elastic portion to stabilize the backward movement of the pricking needle. Therefore, the track of the pricking needle moving backward can also be made straight. Especially, more straight movement of the pricking needle moving backward directly after the pricking effectively reduces the "hollowing or scratching of the pricked region by the pricking needle", and thereby the pain felt by the pricked subject can be further reduced. It should be noted that the "elastic portion" used in the present invention contributes to the "straight movement" as described above, and thus is not a part that serves to "retract the pricking needle or pull out the needle from the pricked region due to the repulsive force of the elastic portion".

(B) Cushion Effect of Projections "a" and "b"

As mentioned above, after the pricking needle is launched, the projection "a" (137) of the lancet body collides against the projection "b" (257) of the trigger portion. When the projection "a" (137) collides against the projection "b" (257), the pricking needle can be vibrated so that undulating or ruffling thereof is occurred due to the collision (that is, the track of the pricking needle can be deviated). In the invention, the flexible projection "a" (137) indirectly or directly connected to the pricking needle can absorb the undulating or ruffling energy. The "collision between the projection "a" (137) and the projection "b" (257)" can be caused when the tip (150a) of the needle pricks the subject of the blood sampling. The reduction in "displacement" of the pricking needle at the time of pricking can effectively suppress the pain felt by the pricked subject. From a standpoint of absorbing the energy upon the collision by the cushion effect, the projection "a" (137) of the lancet body does not necessarily have flexibility. Alternatively, the projection "b" (257) of the trigger portion may have the flexibility, or both the projection "a" (137) and the projection "b" (257) may have the flexibility.

(C) Cushion Effect of Elastic Portion Upon Pricking

As described in the above (B), the pricking needle is vibrated so that undulating or ruffling thereof is occurred due to the collision between the projection "a" (137) and the projection "b" (257) upon the pricking, which may possibly displace the track of the pricking needle. For this reason, in the invention, the elastic portion 138 indirectly or directly connected to the pricking needle can serve to effectively absorb such undulating or ruffling energy. That is, when a tip 150a of the pricking needle pricks the subject of the blood sampling, the "displacement" of the needle is suppressed by the cushion effect of the elastic portion 138, and thereby the pain upon pricking can be effectively reduced.

(D) Size and Shape of Pricking Opening

The opening end 203 of the lancet holder 200 used in the lancet pricking device of the present invention corresponds to a portion applied to the region to be pricked (for example, a fingertip). In the invention, the opening end 203 is relatively large (that is, larger than the size of a pricking opening generally employed in the technology area of lancet). For example, the inner diameters $ID_1$ and $ID_2$ of the holder at the opening end 203 as shown in FIG. 4 are in the range of about 5 mm to 8 mm. While not wishing to be bound by any theory, a large pricking opening (i.e., the large opening end 203 of the holder) serves to effectively expand the pricked region by a pressing force derived from the holder when such pricking opening is brought into abutment against the pricked region upon pricking. As a result, the "density of pain spots" in the pricked region is supposed to become relatively lower, which makes it possible to reduce the pain felt by the pricked subject upon pricking.

Further, in the pricking device of the invention, the shape of the opening end 203 (in particular, the inner shape of the holder at the opening end) is square or rectangular. Such shape can also effectively contribute to the "reduction in pain upon pricking".

<<Embodiment of Use of Pricking Device>>

In the following, the embodiments of use of the lancet pricking device according to the invention will be described. FIGS. 20 to 29 show the change of the lancet pricking device 400 over time in numerical order. It is noted that the figures indicated by the same figure number among FIGS. 20(a) to 29(a) and FIGS. 20(b) to 29(b) respectively show the state at the same time.

Figure 20:
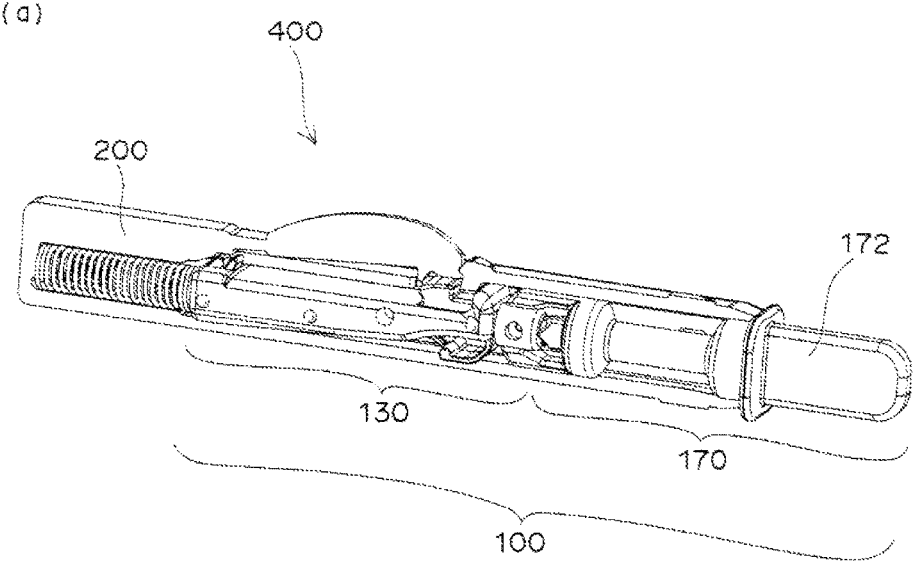
FIGS. 20(*a*) and 20(*b*) are a perspective view and a cross-sectional view schematically showing the embodiment of the lancet pricking device at a point in time before it is used.
Figure 20:
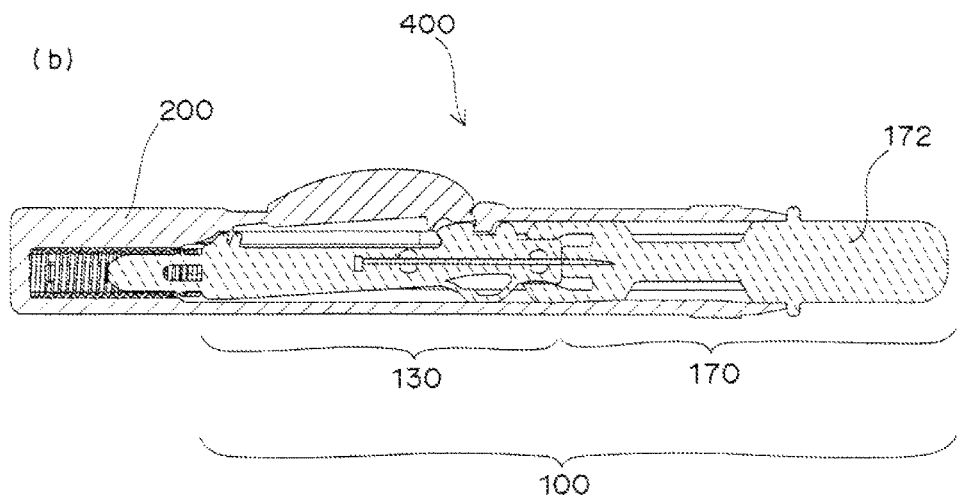
Figure 21:
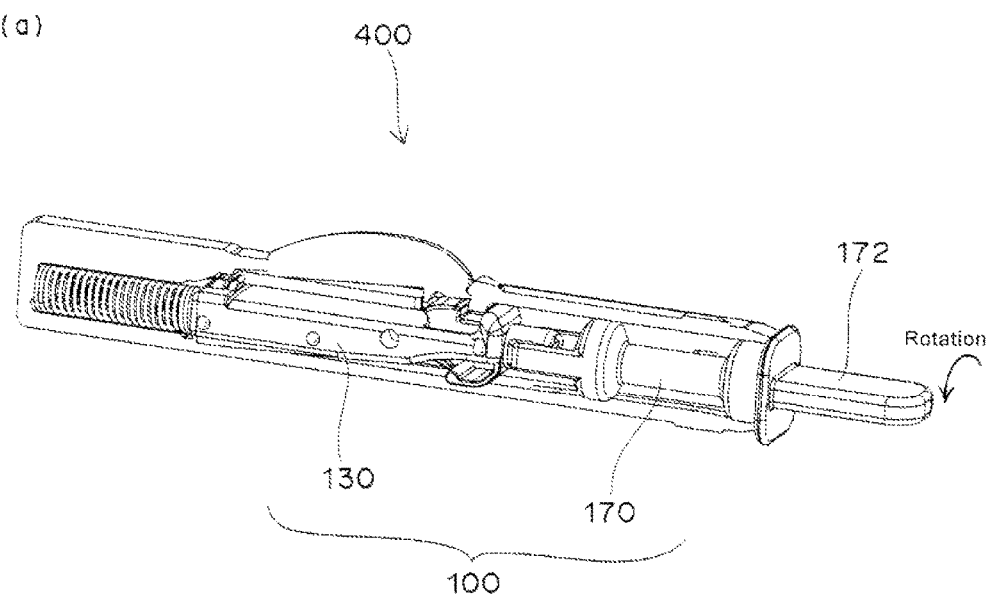
FIGS. 21(*a*) and 21(*b*) are a perspective view and a cross-sectional view schematically showing the embodiment of the lancet pricking device at a point in time when the lancet cap is being removed.
Figure 21:
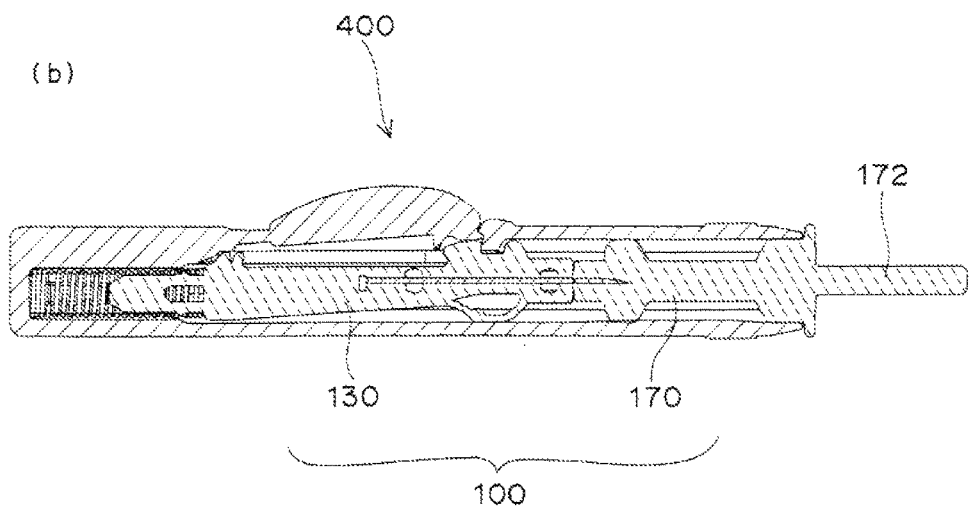
Figure 22:
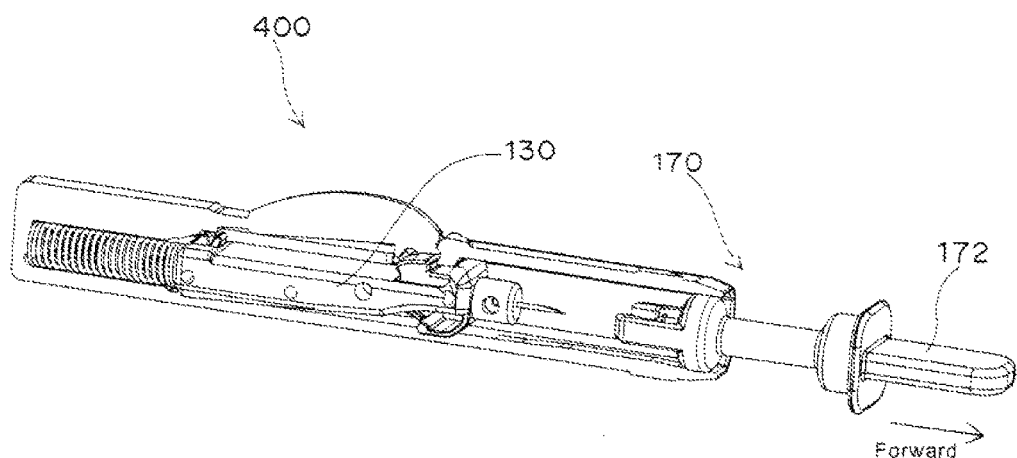
FIGS. 22(*a*) and 22(*b*) are a perspective view and a cross-sectional view schematically showing the embodiment of the lancet pricking device at a point in time just after the lancet cap is removed.
Figure 22:
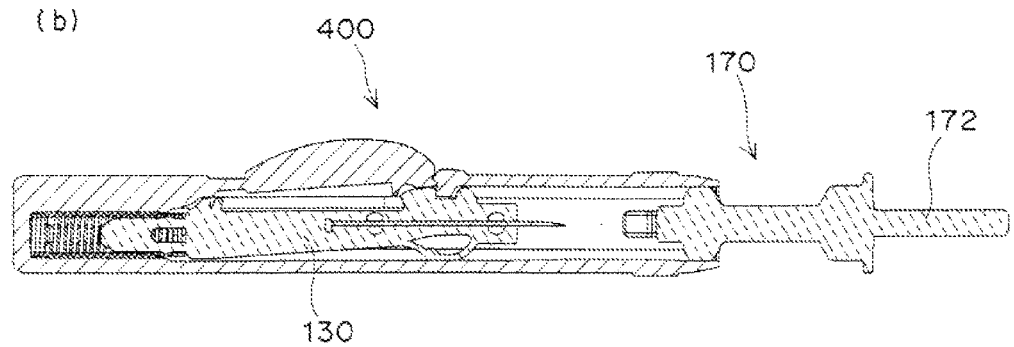
Figure 23:
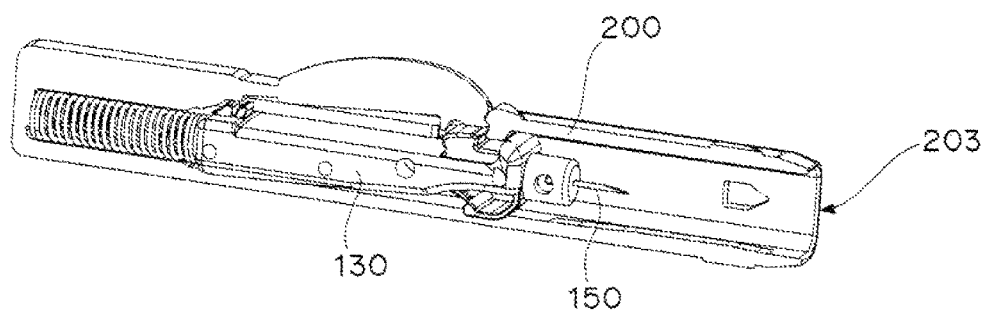
FIGS. 23(*a*) and 23(*b*) are a perspective view and a cross-sectional view schematically showing the embodiment of the lancet pricking device at a point in time just before the pricking operation is performed.
Figure 23:
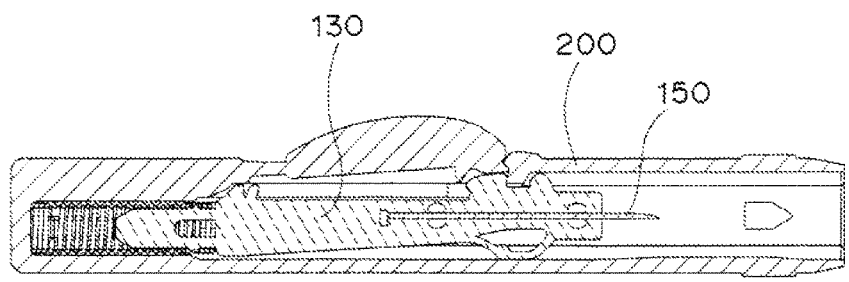
Figure 24:
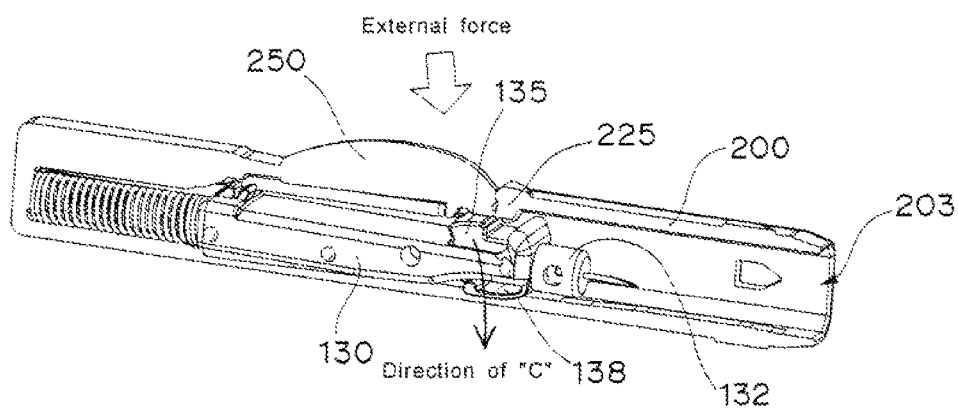
FIGS. 24(*a*) and 24(*b*) are a perspective view and a cross-sectional view schematically showing the embodiment of the lancet pricking device at a point in time when the trigger portion is pressed.
Figure 24:
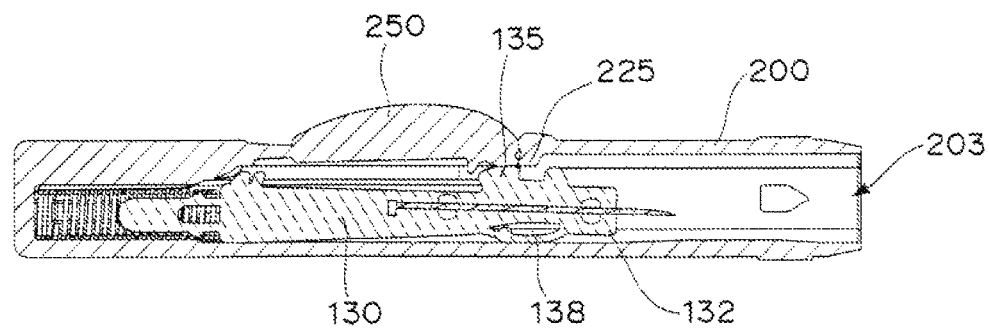
Figure 25:
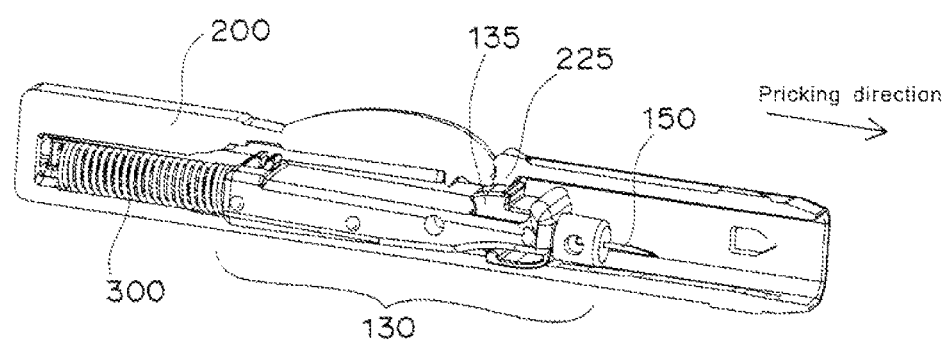
FIGS. 25(*a*) and 25(*b*) are a perspective view and a cross-sectional view schematically showing the embodiment of the lancet pricking device at a point in time when the securing of the lancet body is released.
Figure 25:
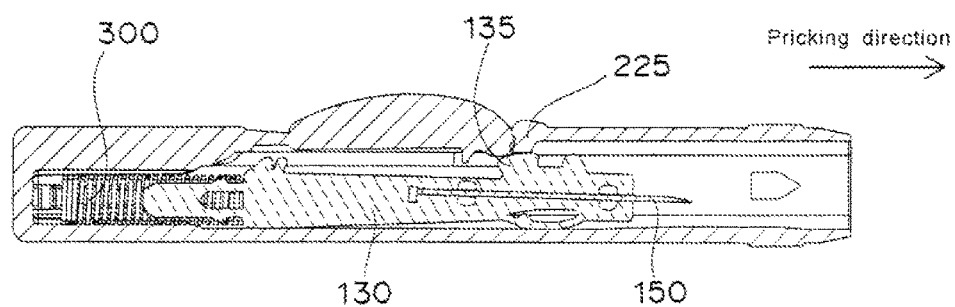
Figure 26:
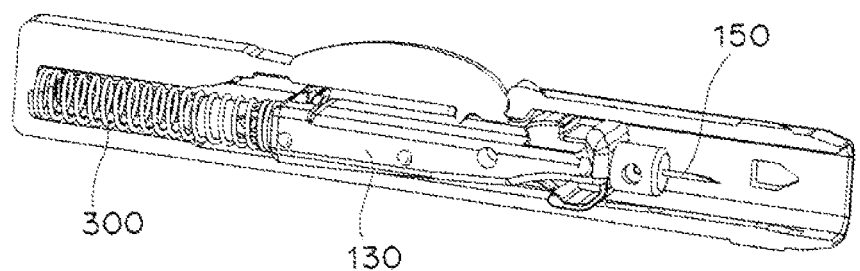
FIGS. 26(*a*) and 26(*b*) are a perspective view and a cross-sectional view schematically showing the embodiment of the lancet pricking device at a point in time just after the lancet body is launched.
Figure 26:
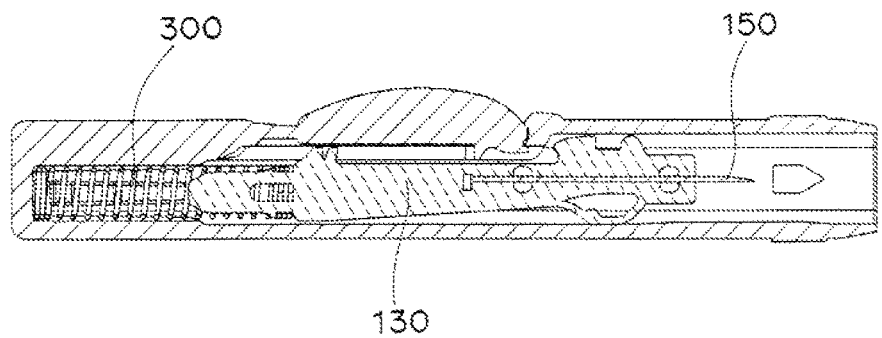

The lancet pricking device 400 of the present invention before the pricking operation is shown in FIG. 20. First, as shown in FIGS. 20 to 22, the lancet cap 170 is removed from the lancet 100. The lancet cap 170 is removed preferably by twisting the lancet cap 170. Specifically, as shown in FIG. 21, the lancet cap 170 (in particular, the holding portion 172) is rotated to break the "contact between the lancet body 130 and the lancet cap 170", and thereafter the lancet cap 170 is pulled out forwardly as shown in FIG. 22. In other words, one hand holds the lancet holder 200 from the outside, and the fingers of the other hand pull the holding portion 172 of the lancet cap 170 while twisting it. As a result, the pricking needle 150 is exposed in the lancet body 130 within the lancet holder 200 (see FIG. 23). Then, after the opening end 203 of the lancet holder 200 is applied to the predetermined region to be pricked (e.g., a fingertip), the trigger portion 250 is pushed toward the inside of the holder (see FIG. 24). The pushing of the trigger portion 250 causes the lancet body 130 to warp due to a pressing action of the pushed trigger portion 250, and thereby the securing of the lancet body 130 to the lancet holder 200 is released. Specifically, since the pushed trigger portion 250 serves to press the engagement part 135 of the lancet body 130 in the direction "C" as shown in FIG. 24, the elastic portion 138 of the lancet body 130 is caused to warp, and thereby causing the tip section 132 of the lancet body to incline from the center axis of the holder. As a result, the securing state of the "the engagement part 135 of the lancet body 130" with respect to the "engaged part 225 of the lancet holder 200" is released (see FIG. 25). When the securing of the lancet body is released, the compressed spring 300 is expanded to launch the lancet body 130 with the exposed pricking needle 150 in the pricking direction (see FIG. 26).

Figure 27:
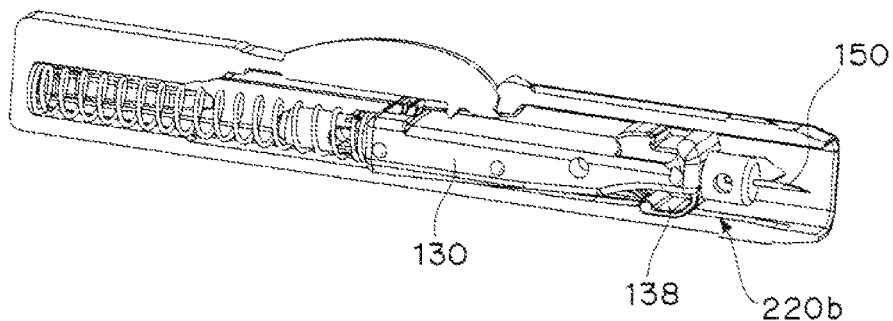
FIGS. 27(*a*) and 27(*b*) are a perspective view and a cross-sectional view schematically showing the embodiment of the lancet pricking device while the lancet body is moving forward.
Figure 27:
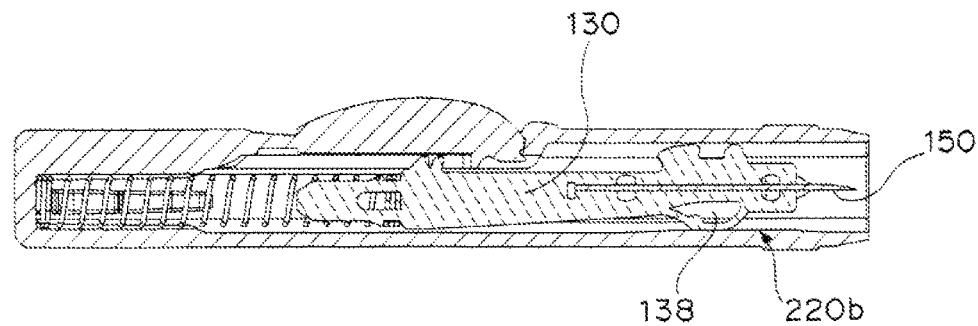

The launched lancet body 130 with the exposed pricking needle 150 moves in the pricking direction while being guided along the inner wall surface of the lancet holder. At this time, as shown in FIG. 27, the elastic portion 138 of the lancet body slides on the inner wall surface 220b of the lancet holder. During such sliding of the elastic portion, as can be seen from the embodiment shown in FIG. 13(c), the elastic portion 138 is caused to warp by receiving the force from the inner wall surface 220b of the lancet holder. As shown in FIG. 13(c), the warping of the elastic portion 138 can be performed by the deformation of the shape of the hollow portion of the elastic portion 138 so that its size is reduced. The warping of the elastic portion 138 can serve to absorb the shock occurred in the lancet body 130 and the pricking needle 150 upon pricking. As a result, the pricking needle 150 can move in the more stable state.

Figure 28:
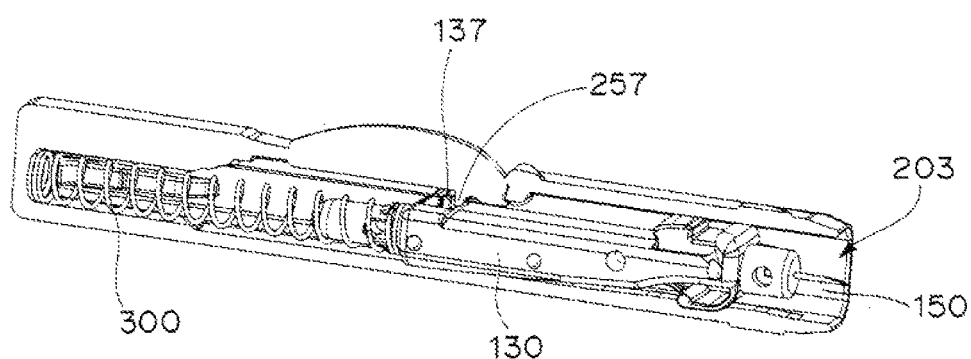
FIGS. 28(*a*) and 28(*b*) are a perspective view and a cross-sectional view schematically showing the embodiment of the lancet pricking device at the time of pricking.
Figure 28:
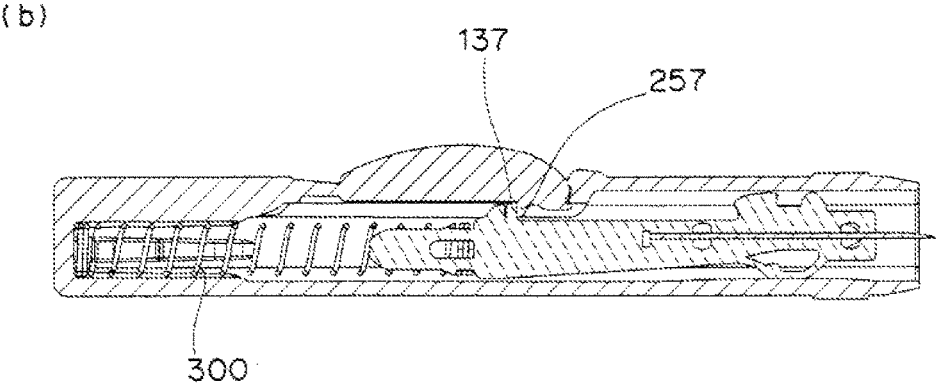
Figure 29:
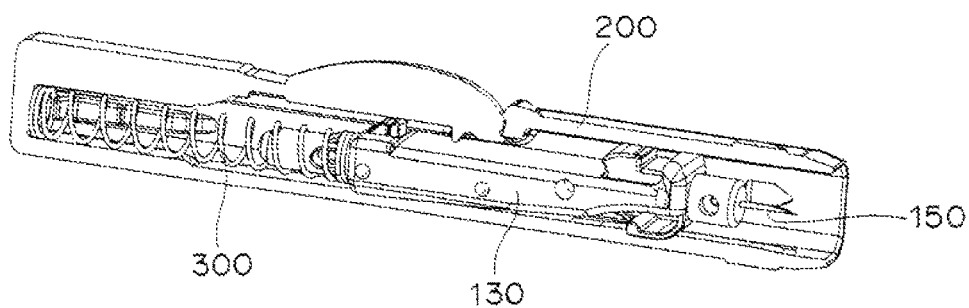
FIGS. 29(*a*) and 29(*b*) are a perspective view and a cross-sectional view schematically showing the embodiment of the lancet pricking device after the pricking operation is performed.
Figure 29:
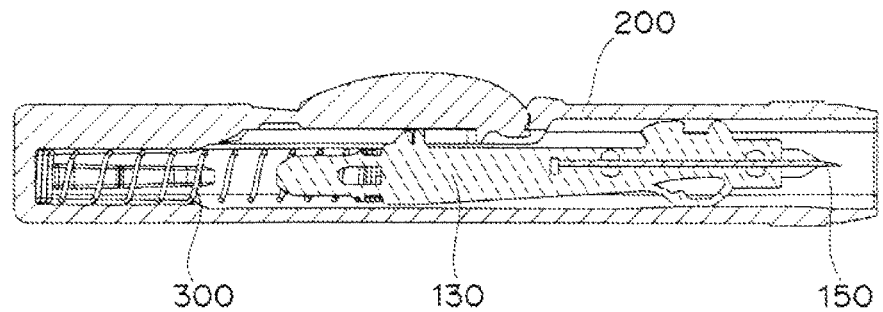
Figure 30:
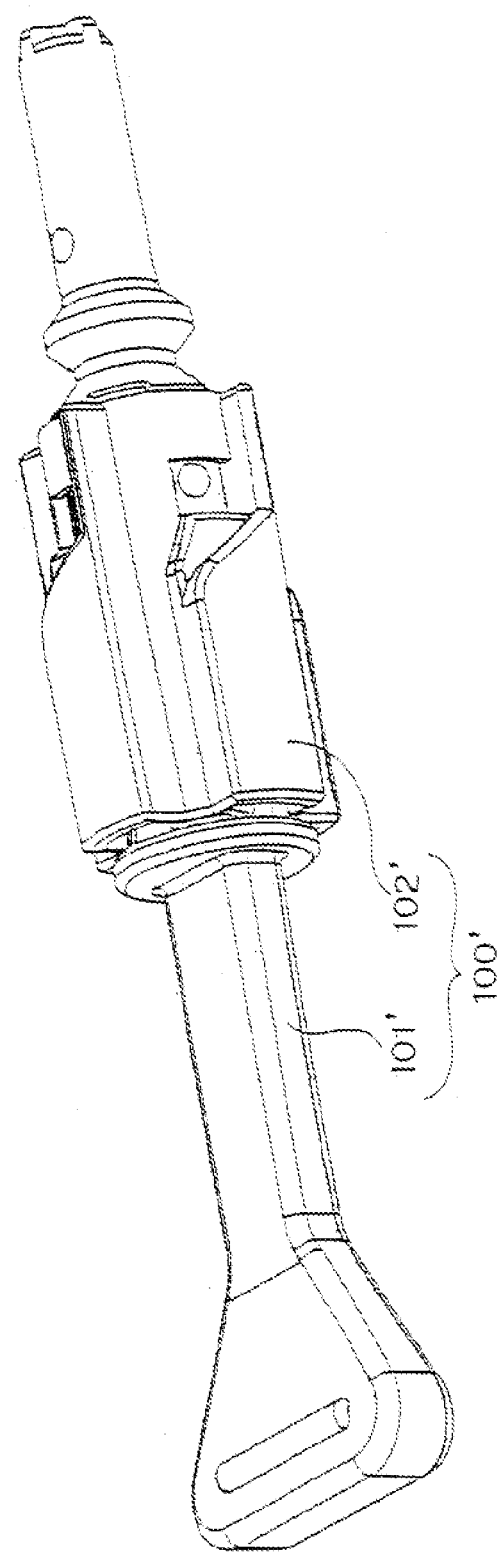
FIG. 30 is a perspective view showing an appearance of a lancet assembly.
Figure 31:
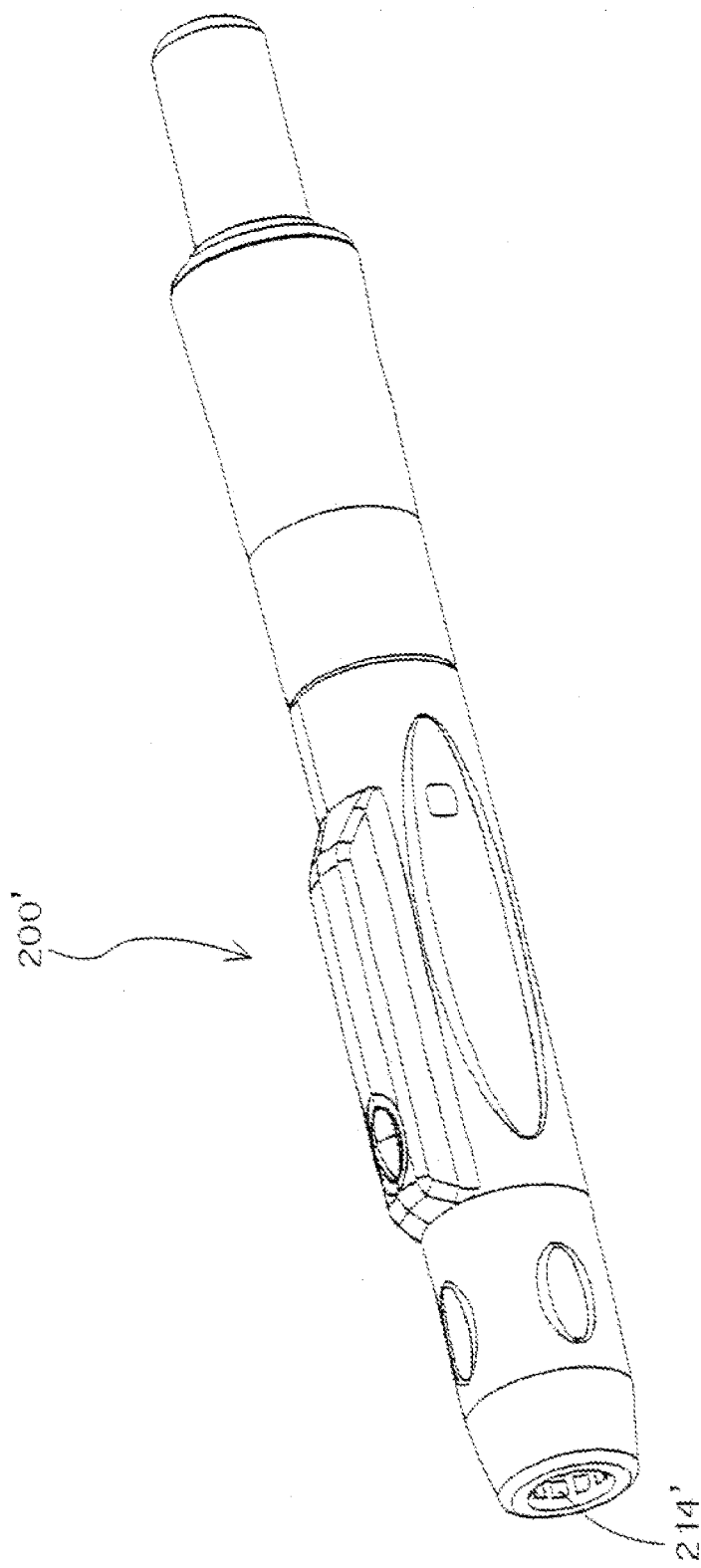
FIG. 31 is a perspective view showing an appearance of an injector.
Figure 32:
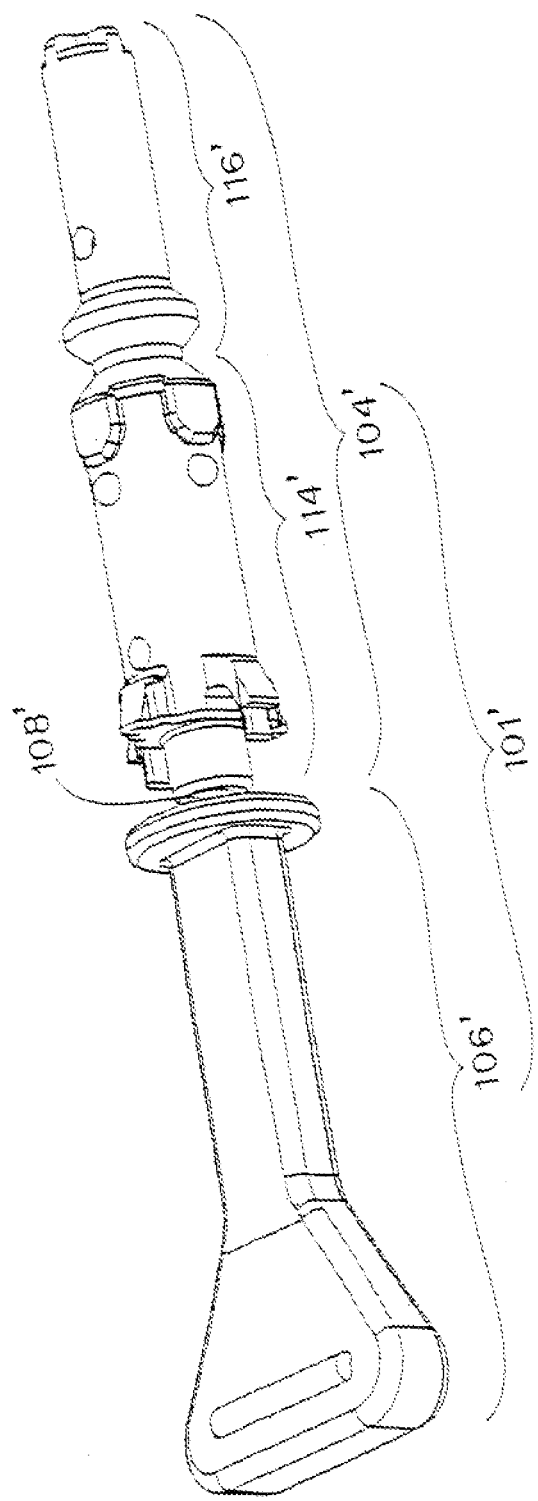
FIG. 32 is a perspective view showing an appearance of a lancet.
Figure 33:
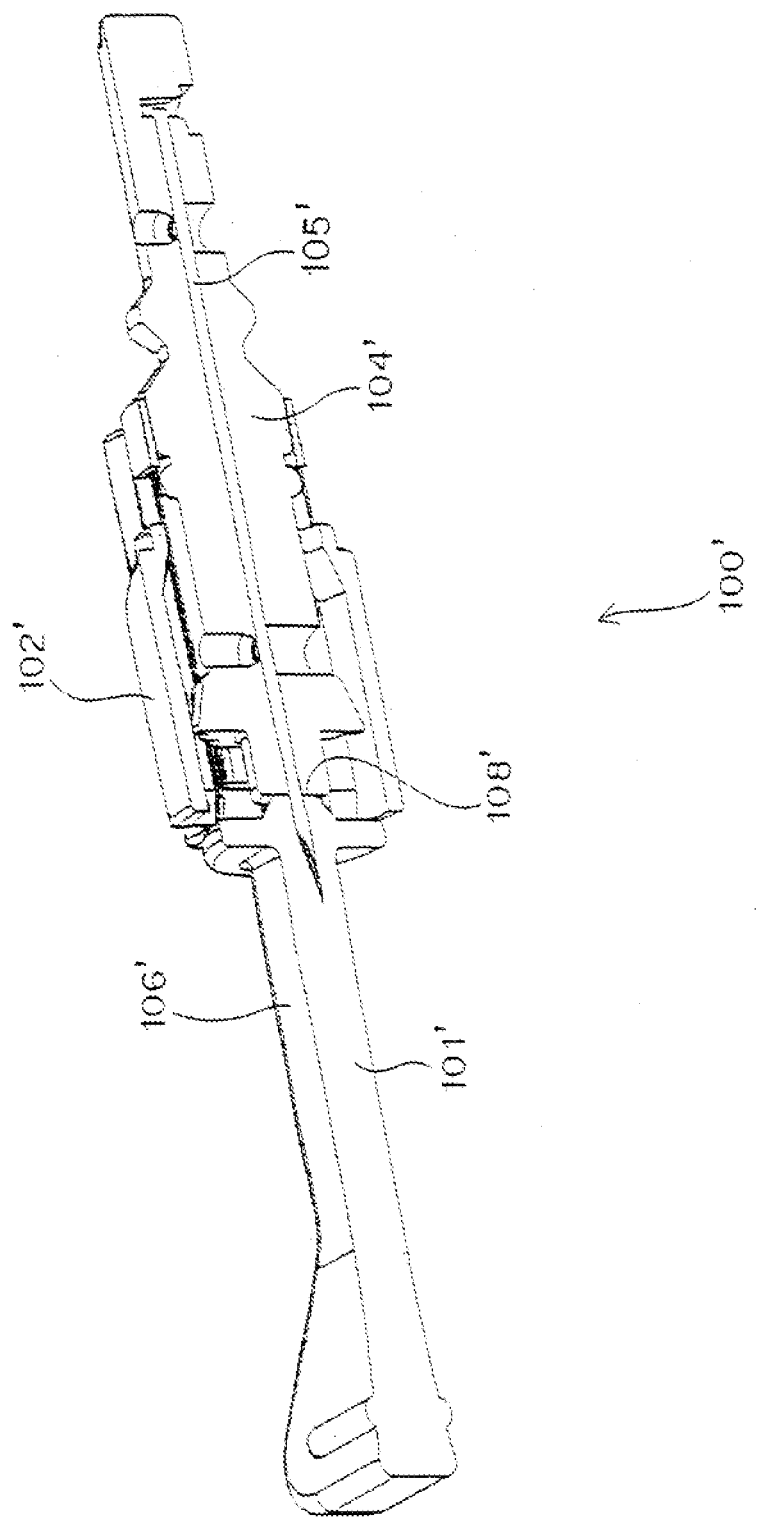
FIG. 33 is a perspective view showing a lancet of FIG. 32, cut away in half so as to make it easy to understand the inside of the lancet.
Figure 34:
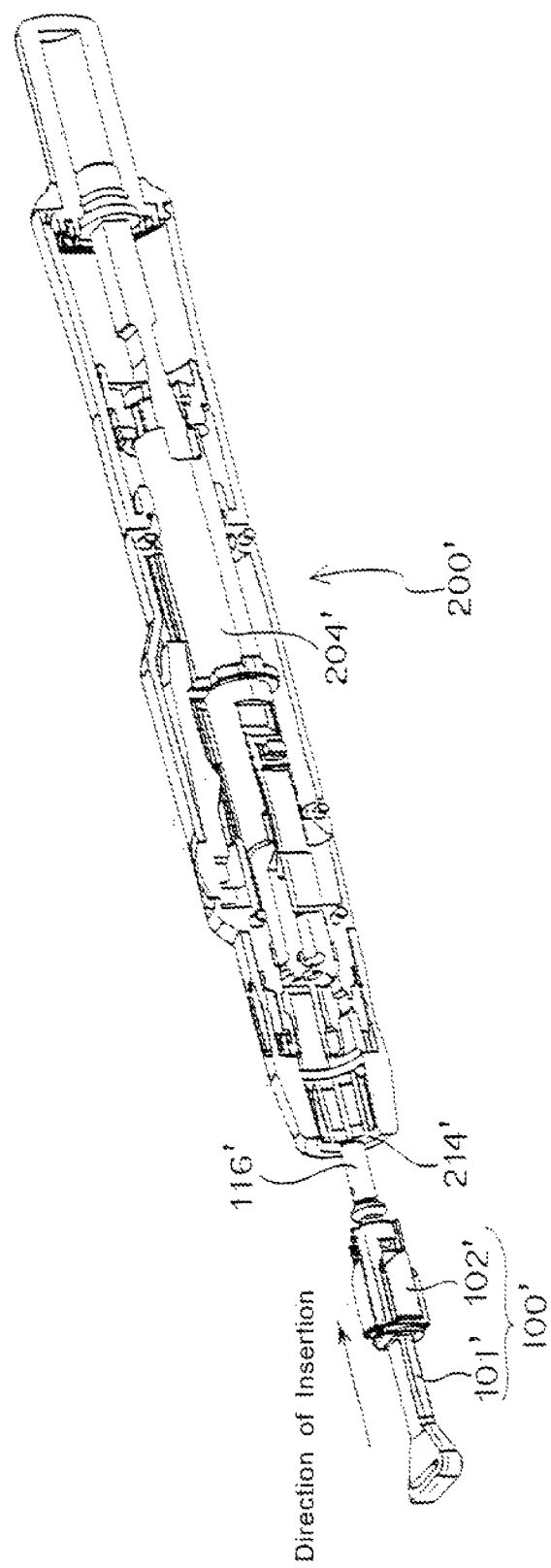
FIG. 34 is a perspective view showing the state before a lancet assembly is loaded into an injector.
Figure 35:
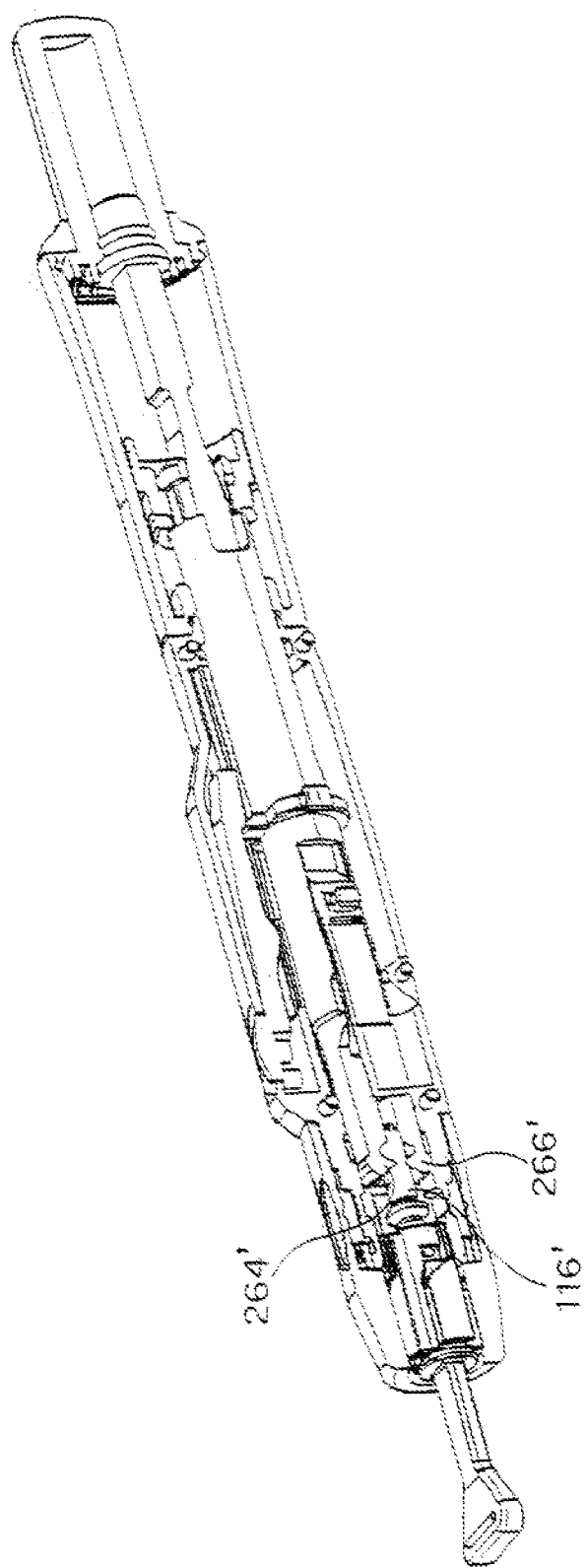
FIG. 35 is a perspective view showing the state in which a lancet is held by the tip of a plunger upon loading a lancet assembly.
Figure 36:
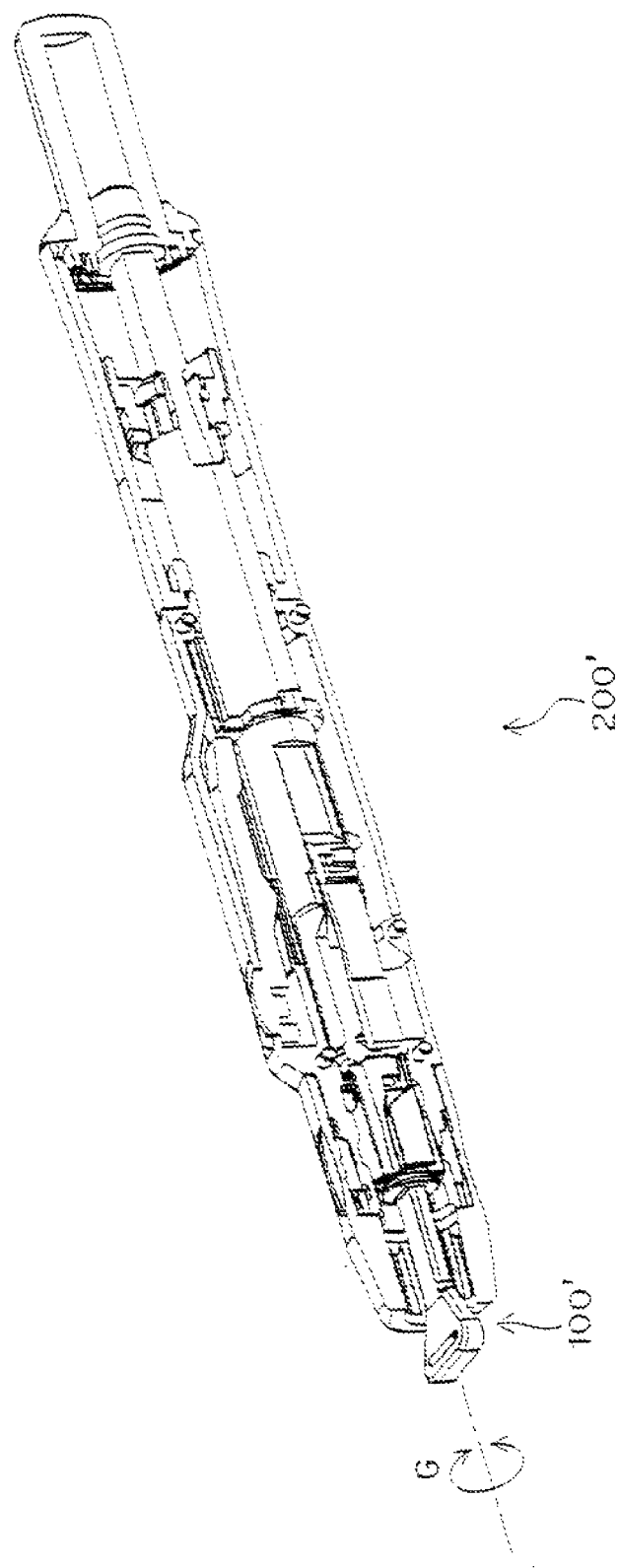
FIG. 36 is a perspective view showing the state of completion of loading a lancet assembly wherein a plunger cannot be retracted any longer.
Figure 37:
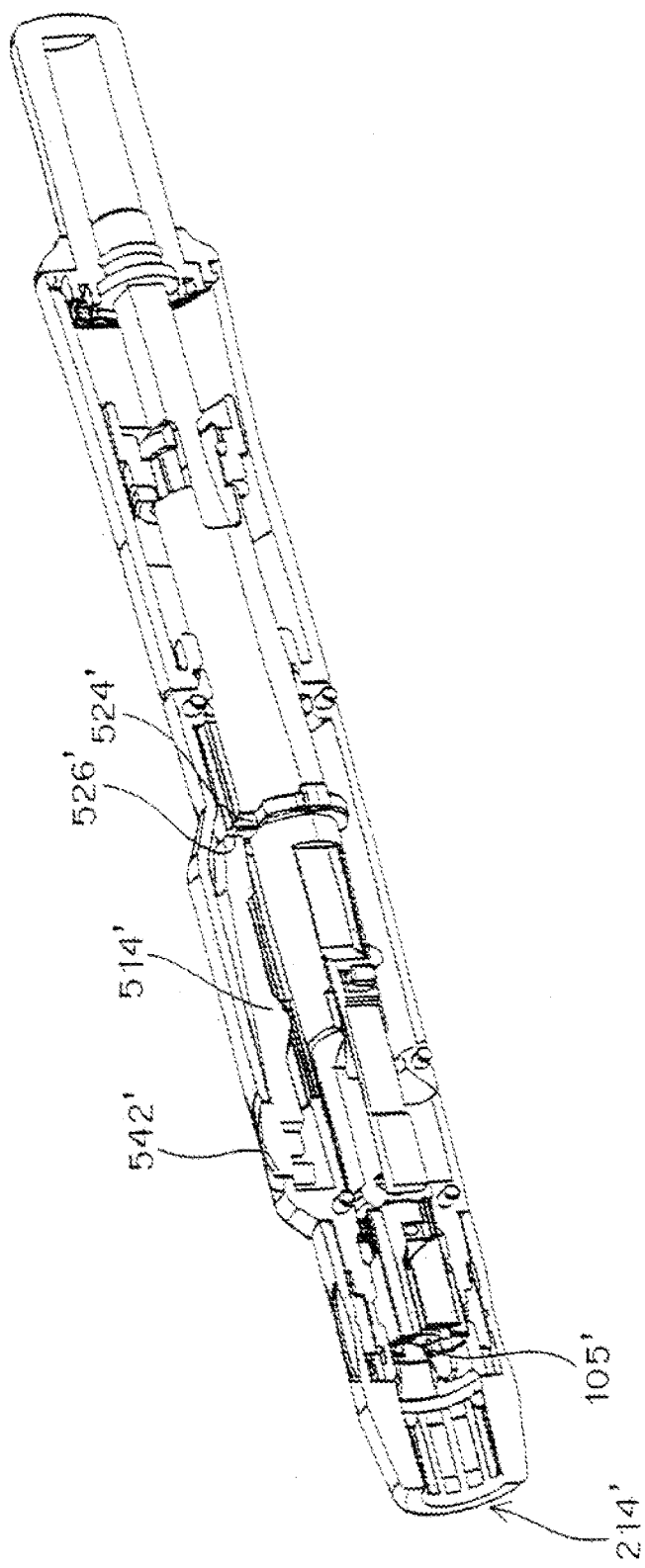
FIG. 37 is a perspective view sowing the state in which a lancet cap has been removed and thus a lancet is ready for pricking.

The pricking needle 150 of the lancet body 130 moving in the pricking direction protrudes from the opening end 203 of the lancet holder, whereby the predetermined region (e.g., fingertip) which is in contact with the opening end 203 is pricked. FIG. 28 shows the embodiment of the pricking device at the time of pricking. As shown in FIG. 28, the projection "a" (137) of the lancet body makes contact with or hits the projection "b" (257) of the trigger portion, and thereby the protruding length of the pricking needle from the opening end of the lancet holder is restricted at the time of pricking. After the pricking, the expanded spring 300 is returned to its original shape, and thereby the pricking needle 150 is quickly retracted. Specifically, since the "lancet body 130 with the pricking needle 150 exposed" has the spring 300 thereto, the lancet body 130 goes back such that it is pulled by the spring, and finally the pricking needle 150 is retracted into the lancet holder 200. The state of the pricking needle after the pricking operation is shown in FIG. 29.

Although a few embodiments of the present invention have been hereinbefore described, the present invention is not limited to these embodiments. It will be readily appreciated by those skilled in the art that various modifications are possible without departing from the scope of the present invention. For example, the following modified embodiments are possible.

The elastic portion with its hollow structure has been described. However, the elastic portion is not necessarily limited thereto. The elastic portion may be made of the elastic material as a whole. That is, the elastic portion may be made of material with no hollow structure, the material enabling an elastic deformation thereof. In this regard, the elastic portion is made of rubber or elastomer material, for example.

Although the above embodiments have been described in that the elastic portion provided in the lancet body slides on the inner wall surface of the holder, the present invention is not necessarily limited thereto. In the present invention, the elastic portion may be provided not in the lancet body, but at the inner wall of the holder.

Although the above embodiments have been described in that both the elastic portion exhibiting the straight movement effect, and the elastic portion contributing to the warping of the lancet body are comprised of the same one elastic portion, they may be separately provided.

In order to show the direction (for example, the pricking direction or the like) of the device of the present invention to the user, a direction display (indicator element) may be provided in the lancet holder. For example, an opening 290 having an arrow-like shape as shown in FIG. 1 may be provided.

It should be noted that the present invention as described above includes the following aspects:

First aspect: A lancet pricking device comprising:
  a lancet;
  a launching spring; and
  a lancet holder for housing therein the lancet and the launching spring,
  wherein the lancet comprises a lancet body, a lancet cap and a pricking needle, and the pricking needle is disposed in both the lancet body and the lancet cap;
  wherein the launching spring is attached to the lancet body, and the lancet body is secured by abutting against the lancet holder such that the launching spring is kept compressed before a pricking operation; and
  wherein, when the lancet cap is removed from the pricking needle, the lancet body becomes capable of warping upon being pressed from an outside to cause the securing of the lancet body to be released.

Second aspect: The lancet pricking device according to First aspect, wherein the releasing of the secured lancet body causes the compressed spring to expand, and thereby forcing the lancet body with the exposed pricking needle to be launched in the pricking direction.

Third aspect: The lancet pricking device according to First or Second aspect, wherein the lancet cap comprises a wing portion; and
  wherein, when the pricking needle is covered with the lancet cap, at least a part of the wing portion is located between the lancet body and an inner wall surface of the lancet holder, and thereby the warping of the lancet body upon being pressed is prevented.

Fourth aspect: The lancet pricking device according to any one of First to Third aspects, wherein the lancet body is provided with an elastic portion; and
  wherein the elastic portion is caused to warp when the lancet body warps.

Fifth aspect: The lancet pricking device according to any one of First to Third aspects, wherein the lancet body is provided with an elastic portion; and
  the lancet body is launched to move in the pricking direction, the elastic portion of the moving lancet body slides on an inner wall surface of the lancet holder.

Sixth aspect: The lancet pricking device according to Fourth or Fifth aspect, wherein the elastic portion has a hollow structure.

Seventh aspect: The lancet pricking device according to any one of Fourth to Sixth aspects, wherein the inner wall surface of the lancet holder is provided with a tapered portion; and
  wherein the elastic portion of the moving lancet body slides on the tapered portion.

Eighth aspect: The lancet pricking device according to any one of First to Seventh aspects, wherein the lancet holder is provided with a trigger portion;
  wherein, when the trigger portion is pushed into the lancet holder after the removal of the lancet cap, the lancet body is forced to warp by a pressing force derived from the pushed trigger portion, which results in a ceasing of engagement between an engagement part of the lancet body and an engaged part of the lancet holder, both of which are provided for securing the lancet body to the holder.

Ninth aspect: The lancet pricking device according to Eighth aspect, wherein, while an inward pushing of the trigger portion is performed in the pricking operation, at least a part of a periphery of the trigger portion abuts against an edge portion defining a trigger opening of the lancet holder, and thereby the warping of the lancet body is restricted.

Tenth aspect: The lancet pricking device according to Eight or Ninth aspect, wherein the lancet body is provided with a projection "a" for adjusting a pricking depth, whereas the trigger portion is provided with a projection "b" for adjusting the pricking depth;
  wherein, upon the pricking, the projection "a" of the lancet body makes contact with the projection "b" of the trigger portion, and thereby a protruding length of the pricking needle from an opening end of the lancet holder is restricted.

Eleventh aspect: The lancet pricking device according to Tenth aspect, wherein the projection "a" is capable of warping in a forward-backward direction.

Twelfth aspect: The lancet pricking device according to any one of Ninth to Eleventh aspects when appendant to Eighth aspect, wherein, at a point in time before the pricking operation is performed, a forward side (front face) of the engagement part of the lancet body is in engagement with a backward side (rear face) of the engaged part of the lancet holder; and
  at a point in time after the pricking operation is performed, a backward side (rear face) of the engagement part of the lancet body is capable of making contact with a forward side (front face) of the engaged part of the lancet holder such that a backward movement of the lancet body is restricted, and thereby the lancet body cannot be returned to its pre-pricking state.

INDUSTRIAL APPLICABILITY

The lancet pricking device according to the present invention is prevented from being re-used, and also has an improved pricking pathway of the needle thereof. Accordingly, the lance pricking device of the present invention can be not only used to take out blood from a patient with diabetes, but also suitably used for various other applications that need the blood sampling.

CROSS REFERENCE TO RELATED PATENT APPLICATION

The present application claims the right of priority of Japan patent application No. 2009-209493 (filing date: Sep. 10, 2009, title of the invention: LANCET PRICKING DEVICE), the whole contents of which are incorporated herein by reference.

BRIEF EXPLANATION OF REFERENCE NUMERALS

100 Lancet
130 Lancet body
132 Tip section of lancet body
133 Rear end of lancet (spring-attachment portion)
135 Engagement part of lancet body
135a Backward side (rear face) of engagement part of lancet body 135b Forward side (front face) of engagement part of lancet body
136 Boss provided on side face of lancet body
137 Projection "a" of lancet body for adjusting a pricking depth at the time of pricking
137a Root of projection "a"
138 Elastic portion
138a Cavity or hollow of elastic portion
138b Protrusion on elastic portion's inner surface which forms cavity thereof
139 Auxiliary projection
150 Pricking needle
150a Tip of pricking needle
170 Lancet Cap
171 Wing portion of lancet cap
171a Tip of wing portion
200 Lancet holder
203 Opening end of lancet holder
220a Rear end sided-inner wall surface of lancet holder
220b Inner wall surface of lancet holder
220b' Tapered portion provided at inner wall surface of lancet holder
220c Chamfered portion at corner of inner wall of lancet holder
221 Spring-attachment portion provided in the inside of lancet holder
225 Engaged part of lancet holder
225a Forward side of engaged part of lancet holder
225b Backward side of engaged part of lancet holder
226 Edge surface defining a trigger opening of lancet holder
250 Trigger portion
250a Rear end of trigger portion
250b Front end of trigger portion
252 Expanded part of trigger portion
257 Projection "b" of lancet body for adjusting a pricking depth at the time of pricking
258 Edge portion defining a trigger opening of lancet holder
290 Indicator opening
300 Launching spring
400 Pricking device
100' Lancet assembly
101' Lancet
102' Protective cover
104' Lancet body
105' Pricking needle
106' Lancet cap
108' Weakened part
114' Front part of lancet body
116' Rear part of lancet body
200' Injector
204' Plunger
214' Front end opening of injector
264', 266' Tips of plunger
514' Trigger component
524' Protrusion provided in plunger
526' Rear end portion of trigger component
542' Press portion of trigger component

The invention claimed is:

1. A lancet pricking device comprising:
a lancet;
a launching spring; and
a lancet holder for housing therein the lancet and the launching spring,
wherein the lancet comprises a lancet body, a lancet cap and a pricking needle, and the pricking needle is disposed in both the lancet body and the lancet cap,
wherein the launching spring is attached to the lancet body, and the lancet body is secured by abutting against the lancet holder such that the launching spring is kept compressed before a pricking operation,
wherein, when the lancet cap is removed, the lancet body becomes capable of warping upon being pressed from an outside to cause the secured lancet body to be released,
wherein the lancet body is provided with an elastic portion, and the elastic portion warps when the warping of the lancet body is performed, such that a tip section of the lancet body inclines,
wherein the lancet body is launched to move in a pricking direction, and
wherein the elastic portion of the moving lancet body slides on an inner wall surface of the lancet holder.

2. The lancet pricking device according to claim 1, wherein the lancet cap comprises a wing portion, and
wherein, when the pricking needle is covered with the lancet cap, at least a part of the wing portion is positioned between the lancet body and the inner wall surface of the lancet holder, and thereby the warping of the lancet body upon being pressed is prevented.

3. The lancet pricking device according to claim 1, wherein the elastic portion has a hollow structure.

4. The lancet pricking device according to claim 1, wherein the inner wall surface of the lancet holder is provided with a tapered portion, and
wherein the elastic portion of the moving lancet body slides on the tapered portion.

5. The lancet pricking device according to claim 4, wherein the tip section of the lancet body inclines in a direction toward the tapered portion.

6. The lancet pricking device according to claim 4, wherein the lancet holder includes a first end and a second end opposite the first end,
wherein the first end of the lancet holder contains the launching spring, and
wherein the tapered portion is closer to the second end of the lancet holder than the first end of the lancet holder.

7. The lancet pricking device according to claim 1, wherein the lancet holder is provided with a trigger portion, and
wherein, when the trigger portion is pushed into the lancet holder after the removal of the lancet cap, the lancet body is forced to warp by a pressing force derived from the pushed trigger portion, which results in a ceasing of engagement between an engagement part of the lancet body and an engaged part of the lancet holder, both of which are provided for securing the lancet body.

8. The lancet pricking device according to claim 7, wherein, when the trigger portion is inwardly pushed in the pricking operation, at least a part of a periphery of the trigger portion abuts against an edge portion defining a trigger opening of the lancet holder, and thereby the warping of the lancet body is restricted.

9. The lancet pricking device according to claim 7, wherein the lancet body is provided with a projection for adjusting a pricking depth, and the trigger portion is provided with a projection for adjusting the pricking depth,
wherein, upon pricking, the projection of the lancet body makes contact with the projection of the trigger portion, and thereby a protruding length of the pricking needle from an opening end of the lancet holder is restricted.

10. The lancet pricking device according to claim 9, wherein the projection of the lancet body is capable of warping in a forward-backward direction.

11. The lancet pricking device according to claim 7, wherein, at a point in time before the pricking operation is performed, a forward side of the engagement part of the lancet body is in engagement with a backward side of the engaged part of the lancet holder, and
- at a point in time after the pricking operation is performed, a backward side of the engagement part of the lancet body is capable of making contact with a forward side of the engaged part of the lancet holder such that a backward movement of the lancet body is restricted, and thereby the lancet body cannot be returned to a pre-pricking state of the lancet body.

12. The lancet pricking device according to claim 1, wherein the tip section of the lancet body is a portion of the lancet body closest to a tip of the pricking needle.

\* \* \* \* \*